US008523950B2

United States Patent
Dees et al.

(10) Patent No.: US 8,523,950 B2
(45) Date of Patent: Sep. 3, 2013

(54) ANATOMICAL MOTION HINGED PROSTHESIS

(75) Inventors: Roger Ryan Dees, Senatobia, MS (US); Paul Charles Crabtree, Jr., Hesbit, MS (US); Jonathan Kirk Nielsen, San Clemente, CA (US)

(73) Assignee: Smith & Nephew, Inc., Memphis, TN (US)

( * ) Notice: Subject to any disclaimer, the term of this patent is extended or adjusted under 35 U.S.C. 154(b) by 718 days.

(21) Appl. No.: 12/307,102

(22) PCT Filed: Jun. 30, 2007

(86) PCT No.: PCT/US2007/072611
§ 371 (c)(1),
(2), (4) Date: Feb. 3, 2010

(87) PCT Pub. No.: WO2008/005905
PCT Pub. Date: Jan. 10, 2008

(65) Prior Publication Data
US 2010/0131070 A1    May 27, 2010

Related U.S. Application Data

(60) Provisional application No. 60/806,383, filed on Jun. 30, 2006.

(51) Int. Cl.
*A61F 2/38* (2006.01)
(52) U.S. Cl.
USPC .................. 623/20.28; 623/20.24; 623/20.31
(58) Field of Classification Search
USPC ........................................... 623/20.24, 20.28
See application file for complete search history.

(56) References Cited

U.S. PATENT DOCUMENTS 3,824,630 A   7/1974  Johnston
3,837,009 A   9/1974  Walker
(Continued)

FOREIGN PATENT DOCUMENTS

DE      3022668 A1    12/1981
DE      4102509 C2     6/1996
(Continued)

OTHER PUBLICATIONS

English-Language Translation of EP472475, translated on May 23, 2012, with certification of translation, 11 pages.

(Continued)

*Primary Examiner* — Bruce E Snow
*Assistant Examiner* — Melissa Hoban
(74) *Attorney, Agent, or Firm* — Fish & Richardson P.C.

(57) ABSTRACT

A hinged knee prosthesis (10) comprises a tibial component (16) and a femoral component (14). The tibial component (16) is configured to attach to a tibia. The tibial component has a bearing surface (128). The femoral component (14) is configured to hingedly attach to the tibial component (16) and rotate relative to the tibial component (16). The femoral component (14) comprises a medial condyle (30) and a lateral condyle (32). The medial and lateral condyles (30 and 32) have an eccentric sagittal curvature surface (50) configured to rotate and translate on the bearing surface (128) of the tibial component (16). A method of rotating a hinged knee (10) through a range of flexion is provided. The method fixedly attaches a femoral component (14) to a tibial component (16). Axial rotation of the femoral component (14) is induced relative to the tibial component (16) when the hinged knee (10) is flexed.

20 Claims, 21 Drawing Sheets

(56) References Cited

U.S. PATENT DOCUMENTS

| | | |
|---|---|---|
| 3,934,272 A | 1/1976 | Wearne et al. |
| 4,213,209 A | 7/1980 | Insall et al. |
| 4,262,368 A | 4/1981 | Lacey |
| 4,301,553 A | 11/1981 | Noiles |
| 4,358,859 A | 11/1982 | Schurman et al. |
| 4,462,120 A | 7/1984 | Rambert et al. |
| 4,538,305 A | 9/1985 | Engelbrecht et al. |
| 4,662,889 A | 5/1987 | Zichner et al. |
| 4,770,663 A | 9/1988 | Hanslik et al. |
| 4,834,758 A | 5/1989 | Lane et al. |
| 4,865,606 A | 9/1989 | Rehder |
| 5,147,405 A | 9/1992 | Van Zile et al. |
| 5,147,406 A | 9/1992 | Houston et al. |
| 5,181,925 A | 1/1993 | Houston et al. |
| 5,236,461 A | 8/1993 | Forte |
| 5,314,481 A | 5/1994 | Bianco |
| 5,358,527 A | 10/1994 | Forte |
| 5,370,701 A | 12/1994 | Finn |
| 5,405,398 A | 4/1995 | Buford, III et al. |
| 5,411,555 A | 5/1995 | Nieder |
| 5,413,607 A * | 5/1995 | Engelbrecht et al. ...... 623/20.24 |
| 5,549,689 A | 8/1996 | Epstein et al. |
| 5,702,466 A | 12/1997 | Pappas |
| 5,755,804 A | 5/1998 | Schmotzer et al. |
| 5,766,257 A | 6/1998 | Goodman et al. |
| 5,782,921 A | 7/1998 | Colleran et al. |
| 5,782,925 A | 7/1998 | Collazo et al. |
| 5,800,552 A | 9/1998 | Forte |
| 5,824,096 A | 10/1998 | Pappas et al. |
| 5,824,102 A | 10/1998 | Buscayret |
| 5,954,770 A | 9/1999 | Schmotzer et al. |
| 6,019,794 A | 2/2000 | Walker |
| 6,068,658 A | 5/2000 | Insall et al. |
| 6,099,570 A | 8/2000 | Livet et al. |
| 6,143,034 A | 11/2000 | Burrows |
| 6,165,223 A * | 12/2000 | Metzger et al. ............ 623/20.27 |
| 6,264,696 B1 * | 7/2001 | Reigner et al. ............. 623/20.24 |
| 6,485,519 B2 | 11/2002 | Meyers et al. |
| 6,770,097 B2 | 8/2004 | Leclercq |
| 6,773,461 B2 | 8/2004 | Meyers et al. |
| 6,984,249 B2 | 1/2006 | Keller |
| 6,986,791 B1 | 1/2006 | Metzger |
| 7,160,330 B2 | 1/2007 | Axelson et al. |
| 7,297,165 B1 | 11/2007 | Kriek |
| 7,572,292 B2 | 8/2009 | Crabtree et al. |
| 7,658,767 B2 | 2/2010 | Wyss |
| 7,871,442 B2 | 1/2011 | Servidio |
| 2001/0001121 A1 | 5/2001 | Lombardo et al. |
| 2002/0103541 A1 | 8/2002 | Meyers et al. |
| 2002/0107576 A1 | 8/2002 | Meyers et al. |
| 2003/0009228 A1 | 1/2003 | Meyers et al. |
| 2004/0143339 A1 | 7/2004 | Axelson et al. |
| 2004/0186584 A1 * | 9/2004 | Keller ........................ 623/20.24 |
| 2004/0249467 A1 * | 12/2004 | Meyers et al. ............. 623/20.24 |
| 2005/0107886 A1 | 5/2005 | Crabtree et al. |
| 2005/0246028 A1 | 11/2005 | Pappas et al. |
| 2008/0119940 A1 | 5/2008 | Otto et al. |
| 2008/0167722 A1 | 7/2008 | Metzger et al. |
| 2009/0088860 A1 | 4/2009 | Romeis et al. |
| 2009/0125114 A1 | 5/2009 | May et al. |
| 2009/0143866 A1 | 6/2009 | Servidio |
| 2010/0016977 A1 | 1/2010 | Masini |

FOREIGN PATENT DOCUMENTS

| | | |
|---|---|---|
| DE | 19915053 A1 | 10/1999 |
| DE | 10012059 C2 | 10/2002 |
| DE | 102005015598 A1 | 9/2006 |
| EP | 69683 A1 | 1/1983 |
| EP | 194326 A1 | 9/1986 |
| EP | 472475 A2 | 2/1992 |
| EP | 472975 B2 | 3/1992 |
| EP | 0336774 | 12/1992 |
| EP | 0420460 | 11/1994 |
| EP | 653194 A1 | 5/1995 |
| EP | 0510299 | 8/1995 |
| EP | 553585 B1 | 11/1995 |
| EP | 716839 A1 | 6/1996 |
| EP | 724868 A1 | 8/1996 |
| EP | 925766 A1 | 6/1999 |
| EP | 1038286 A1 | 9/2000 |
| EP | 0916321 | 6/2003 |
| EP | 0970667 | 12/2003 |
| EP | 1285638 | 11/2005 |
| EP | 1721584 A1 | 11/2006 |
| EP | 1721585 A3 | 12/2006 |
| EP | 0988840 | 5/2007 |
| EP | 2213262 A1 | 8/2010 |
| FR | 2508793 B1 | 10/1983 |
| FR | 2710835 A1 | 4/1995 |
| FR | 2776919 B1 | 9/2000 |
| GB | 1409150 | 10/1975 |
| GB | 2324249 | 10/1998 |
| GB | 2335145 | 9/1999 |
| JP | 49051797 | 5/1974 |
| JP | 8224263 A | 9/1996 |
| JP | 10501155 A | 2/1998 |
| WO | WO9532623 A1 | 12/1995 |
| WO | WO 0113825 | 3/2001 |
| WO | WO03059203 A1 | 7/2003 |
| WO | WO2009056836 A2 | 5/2009 |

OTHER PUBLICATIONS

Brochure entitled Aesculap EnduRo Gekoppelte Knieendoprothese Aesculap Orthopaedics B/Braun Sharing Expertise, 8 pages, known prior to Jul. 16, 2010.

Brochure entitled Aesculap EnduRo Gekoppelte Knieendoprothese Operationstechnik Aesculap Orthopaedics B/Braun Sharing Expertise, 56 pages, known prior to Jul. 16, 2010.

Brochure entitled Aesculap EnduRo Rotating Hinge Knee Endoprothesis Manual Surgical Procedure B/Braun Sharing Expertise, 1 page, known prior to Jul. 16, 2010.

Photograph of Aesculap-B Braun EnduRo Knee—rotating hinge (known prior to Jul. 16, 2010).

Office Action dated May 4, 2007 in related U.S. Appl. No. 10/499,047.

Response dated Nov. 5, 2007 in related U.S. Appl. No. 10/499,047.

Office Action dated Jan. 24, 2008 in related U.S. Appl. No. 10/499,047.

Response dated Apr. 24, 2008 in related U.S. Appl. No. 10/499,047.

Office Action dated May 13, 2008 in related U.S. Appl. No. 10/499,047.

Response dated Aug. 13, 2008 in related U.S. Appl. No. 10/499,047.

Notice of Allowance dated Oct. 8, 2008 in related U.S. Appl. No. 10/499,047.

International Search Report for International Application No. PCT/US2007/072611, mailed Nov. 23, 2007, 4 pages.

First Office Action for Chinese Application No. 20780025036.3, mailed Dec. 7, 2010, 8 pages.

Communication Pursuant to Article 94(3) EPC for European Application No. 07799226.1, mailed Jul. 8, 2010, 4 pages.

International Search Report for International Application No. PCT/US02/41221, mailed Oct. 10, 2003, 3 pages.

Office Action for U.S. Appl. No. 12/353,295, mailed Jun. 19, 2012.

Notice of Reasons for Rejection for Japanese Application No. 2009-518598, mailed Jun. 26, 2012.

Notice of Allowance dated Oct. 8, 2008 in related U.S. Appl. No. 10/499,047, 6 pages.

* cited by examiner

ANATOMICAL MOTION HINGED PROSTHESIS

CROSS-REFERENCE TO RELATED APPLICATIONS

This application is a U.S. National Phase filing of International Application No. PCT/US2007/072611 which claims priority to U.S. Provisional Patent Application 60/806,383 filed Jun. 30, 2006, titled "Anatomical Motion Hinged Prosthesis". The applications are herein incorporated by reference.

BACKGROUND

1. Field

This application relates generally to knee prostheses and, more particularly, the application relates to hinged knee prostheses.

2. Related Art

Most hinged-knee prostheses only provide a mechanical means to restore the joint in a hinge-like function. Other hinged-knee prostheses provide for a more kinematically-correct prostheses; however, they rely mostly on remaining soft tissue to restore normal kinematics to the joint. In most cases, the remaining soft tissue has been compromised and/or missing/removed during surgery. Thus the soft tissue cannot contribute significantly to restoring normal kinematics, particularly anterior/posterior (A/P) translation or normal axial rotation including rotation to the 'screw-home' position. Moreover, the remaining soft tissue may be damaged when restoring normal kinematics by forcing motion of the prostheses.

In prosthetic systems that address axial rotation, current systems address rotation by allowing a rotating platform. Generally, one of the two articulating prostheses (usually the tibial insert or construct) is allowed rotational freedom. This allows the soft tissues to rotate the joint in a more normal fashion. However, most soft tissue has been compromised and cannot reproduce normal or near normal rotation.

A/P translation is a motion that is seldom addressed. In those prostheses that do address A/P translation, a cam mechanism against the joint-linking mechanism (usually a post) or against the tibial articular geometry is used to force the tibia anteriorly relative to the distal femur as the knee flexes. This method of A/P translation is common in a primary total knee arthroplasty (TKA) by the use of a cam and post method in which the cam is on the femoral articulating prosthesis and the post is found on the tibial articulating prosthesis. This is commonly referred to as a posterior or cruciate stabilized knee implant. These hinged knees generally focus forces on a small area (such as a cam with point and/or line contact and post), which may increase wear and decrease the life span of the implant.

In U.S. Pat. Nos. 5,358,527 and 5,800,552, A/P translation is allowed through flexion, yet the hinged knee does not control and/or maintain a constant limit on A/P translation. In other words, the femoral can be flexed and can translate posteriorly when contact to the tibial bearing surface is not maintained. Thus the femoral component does not maintain contact with the tibial component when A/P translation occurs.

There remains a need in the art for kinematically-correct prostheses including A/P translation and/or normal axial rotation. In addition, there remains a need for kinematically-correct prostheses that reduce wear on the prosthesis and reduce forces on the remaining soft tissue.

SUMMARY

The disclosure provides a hinged knee prosthesis comprising a tibial component and a femoral component. The tibial component is configured to attach to a tibia. The tibial component has a bearing surface. The femoral component is configured to hingedly attach to the tibial component and rotate relative to the tibial component. The femoral component comprises a medial condyle and a lateral condyle. The medial and lateral condyles have a sagittal curvature surface configured to induce axial rotation on the bearing surface of the tibial component.

The medial and lateral condyles may have a plurality of eccentric sagittal curvature surfaces configured to rotate on the bearing surface of the tibial component.

The bearing surface of the tibial component is configured with an anterior portion and a posterior portion. The posterior portion of the bearing surface has a portion configured to guide the medial and lateral condyles of the femoral component. Contact points between the femoral component and the tibial component translate in the anterior/posterior direction and rotate axially.

The hinged knee may further comprise an axle hinge pin. The axle hinge pin is located transversely between the medial and lateral condyles. The eccentric sagittal curvature surface has a center of rotation not aligned with the axle hinge pin.

The hinged knee prosthesis may further comprise a post configured to extend from the tibial component to the femoral component. A proximal portion of the post is configured to attach to the axle hinge pin.

The center of rotation of a portion of the eccentric sagittal curvature surface of the medial condyle may not be aligned with the center of rotation of a portion of the eccentric sagittal curvature surface of the lateral condyle. The medial and lateral condyles direct axial rotation of the femoral component relative to the tibial component.

The center of rotation of a portion of the eccentric sagittal curvature surface of the medial condyle may be aligned with the center of rotation of a portion of the eccentric sagittal curvature surface of the lateral condyle, wherein the medial and lateral condyles direct anterior/posterior translation of the femoral component relative to the tibial component.

The medial condyle of the femoral component may further comprise a concentric sagittal curvature surface. The center of rotation of the concentric sagittal curvature surface of the medial condyle is not aligned with the center of rotation of a portion of the eccentric sagittal curvature surface of the lateral condyle. The medial and lateral condyles direct axial rotation of the femoral component relative to the tibial component.

The center of rotation of a first eccentric sagittal curvature surface of the medial condyle may not be aligned with the center of rotation of a first eccentric sagittal curvature surface of the lateral condyle. The medial and lateral condyles direct axial rotation and anterior/posterior translation of the femoral component relative to the tibial component when the first eccentric sagittal curvature surfaces contact the tibial component. The center of rotation of a second eccentric sagittal curvature surface of the medial condyle is aligned with the center of rotation of a second eccentric sagittal curvature surface of the lateral condyle, wherein the medial and lateral condyles direct anterior/posterior translation of the femoral component relative to the tibial component when the second eccentric sagittal curvature surfaces contact the tibial component.

The hinged knee prosthesis may comprise a sleeve configured to receive the post. The sleeve is configured to allow axial rotation of the femoral component relative to the tibial component.

The disclosure provides a method of rotating a hinged knee through a range of flexion. The method fixedly attaches a femoral component to a tibial component. Axial rotation of the femoral component is induced relative to the tibial component when the hinged knee is flexed.

The method may further comprise the step of inducing translation of the femoral component in an anterior/posterior direction relative to the tibial component when the hinged knee is flexed.

The inducing translation step and the inducing axial rotation steps may occur simultaneously.

The inducing axial rotation step may occur through a portion of the range of flexion of the prosthetic knee.

The inducing axial rotation step may occur through a first portion of the range of flexion of the prosthetic knee and a second portion of the range of flexion of the prosthetic knee.

The first portion of the range of flexion may not be adjacent to the second portion of the range of flexion.

The inducing axial rotation step may occur at varying angular velocities as the hinged knee passes through the range of flexion of the knee.

The fixedly attaching step may include connecting a sleeved post to the tibial insert such that a sleeved portion of the sleeved post and a post portion of the sleeved post axially rotate relative to each other. Further the fixedly attaching step may include fixing an axial hinge pin to the sleeved post such that the axial hinge pin transversely connects a medial condyle of the femoral component to the lateral condyle of the femoral component.

The method may further comprise the step of fixing the sleeved portion of the sleeved post to a stem in the tibial component.

The method may further comprise the step of axially displacing the sleeved portion of the sleeved post relative to the post portion of the sleeved post when the hinged knee is flexed.

Thus, kinematically-correct prostheses including A/P translation and/or normal axial rotation may be achieved by the structures in the disclosure. These kinematically-correct prostheses may reduce wear on the prosthesis and reduce forces on the remaining soft tissue. Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments and together with the description, serve to explain the principles of the invention. In the drawings.

DETAILED DESCRIPTION OF THE EMBODIMENTS

Referring to the accompanying drawings in which like reference numbers indicate like elements, FIGS. 1-4 show views of an embodiment of a hinged knee.

Figure 1:
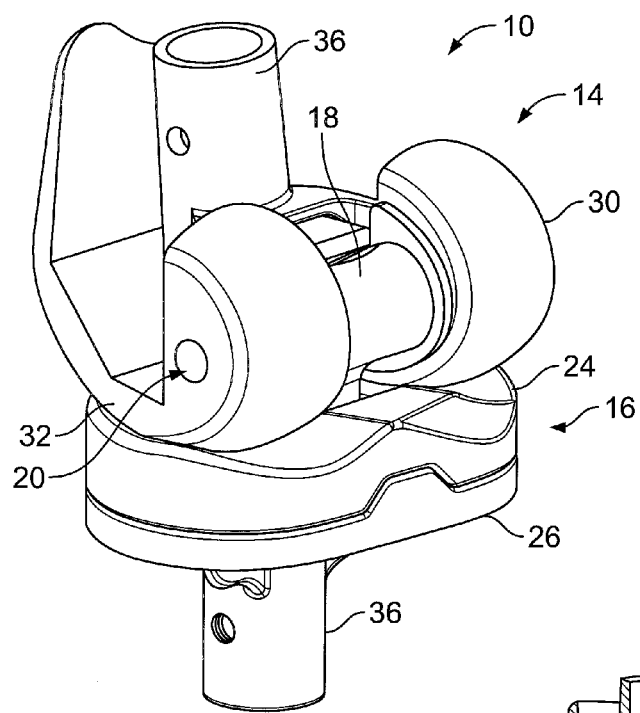
FIG. 1 is an isometric view of an embodiment of a hinged knee.

Turning now to FIG. 1, FIG. 1 is an isometric view of an embodiment of a hinged knee 10. The hinged knee 10 includes a femoral component 14, a tibial component 16, a pin sleeve 18 and a pin 20. The tibial component 16 includes a tibial insert 24 and a tibial base 26. The femoral component 14 includes a medial condyle 30 and a lateral condyle 32. The pin 20 connects the condyles 30 and 32 to the sleeve 18. The sleeve 18 connects to the tibial component through a sleeved post (discussed below).

As the knee flexes, the femoral component 14 rotates relative to the tibial component 16. The femoral component 14 rotates about the pin 20. Axial rotation and anterior/posterior (A/P) translation of the femoral component 14 is urged by the shape of the tibial insert 24 and the condyles 30 and 32. The axial rotation and anterior/posterior (A/P) translation of the femoral component 14 may occur because the pin 20 is able to axial rotate and be axially translated relative to the post and sleeve of the hinged knee 10.

The femoral component 14 and the tibial component 16 are connected to the femur and tibia, respectively. Stems 36 are inserted into the femur and tibia to fix the femoral component and tibial component to the bones. The length and thickness of these stems may be adjusted based upon required fixation, size of the bones, and size of the intramedullary canals in the bones.

Figure 2:
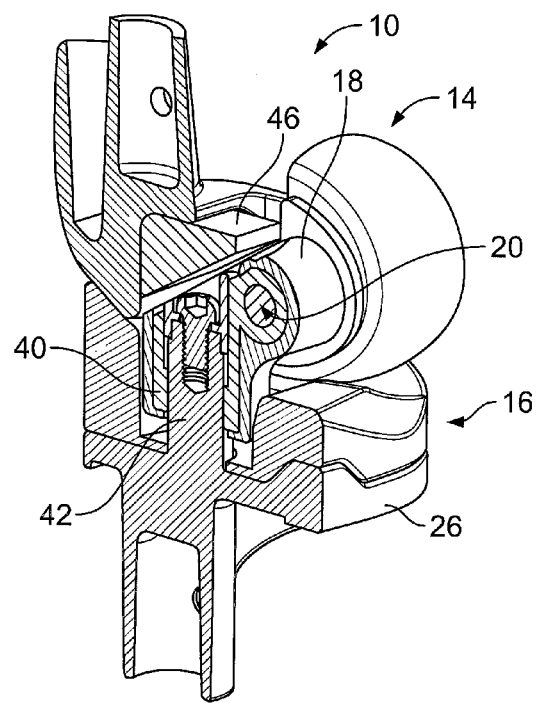
FIG. 2 is a cutaway view of the embodiment of FIG. 1.

Turning now to FIG. 2, FIG. 2 is a cutaway view of the embodiment of FIG. 1. The cutaway is taken in a sagittal plane between the femoral condyles. FIG. 2 shows the pin 20 in the sleeve 18. The sleeve 18 is attached to a post sleeve 40 which surrounds a post 42. The post 42 is attached to the tibial base 26, and may be attached asymmetrically to the tibial base 26. The post sleeve 40 may be axially rotated and axially translated relative to the post 42. The sleeve 18 (and thus the pin 20) may rotate axially and translate axially relative to the tibial component 16. The rotation and translation allow for the femoral component 14 to axially rotate and to translate in the A/P direction. The A/P translation may be accomplished by the condyle surface having a curvature with a center of rotation outside the pin 20. As the femoral component 14 rotates, a bushing 46 stops hyper extension so that the knee may not over extend.

Figure 3:
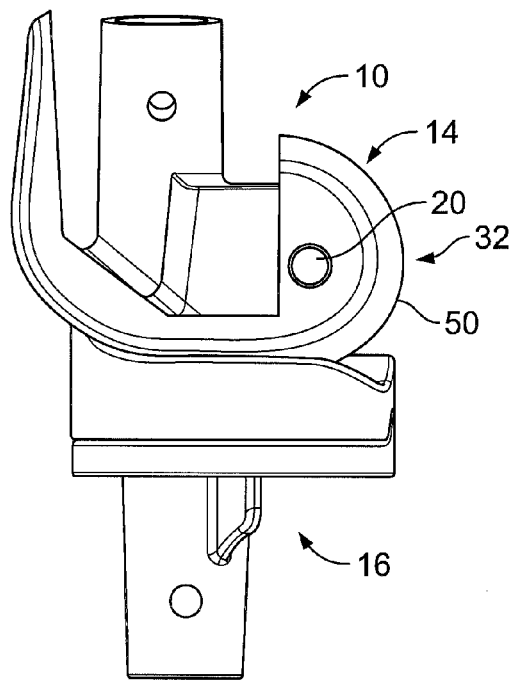
FIG. 3 is a side view of the embodiment of FIG. 1.

Turning now to FIG. 3, FIG. 3 is a side view of the embodiment of FIG. 1. The pin 20 is located posterior to the center of the knee 10. The curve 50 of the condyle 32 is eccentric with respect to the center of rotation of the femoral component 14, which is the pin 20. With respect to the tibial component 16, the pin 20 axially rotates and axially translates as the knee flexes.

Figure 4:
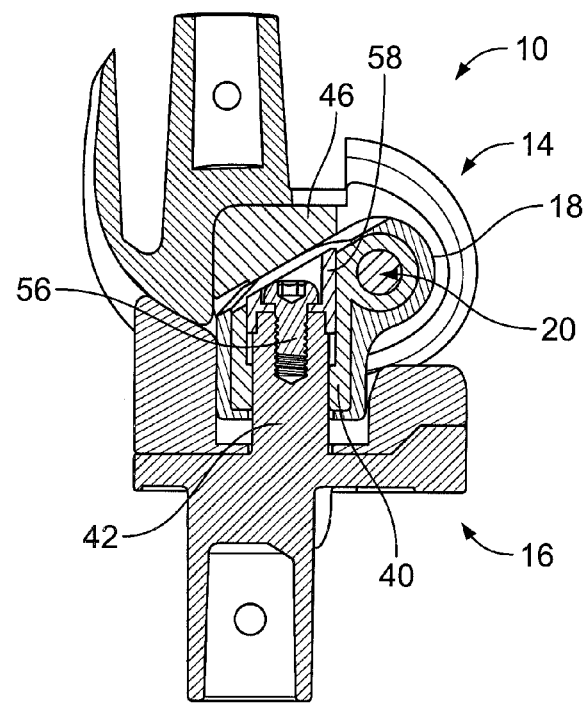
FIG. 4 is a cutaway view of the embodiment of FIG. 3.

Turning now to FIG. 4, FIG. 4 is a cutaway view of the embodiment of FIG. 3. The cutaway is taken along the same sagittal plane of the cutaway in FIG. 2. The cutaway shows the post sleeve 40 and post 42 of the hinged knee 10. A screw 56 fixes a post receiver 58 to the post to lock the post sleeve 40 on the post 42. The post sleeve 40 and pin sleeve 18 then may rotate and translate axially without pulling off the post 42.

Figure 5:
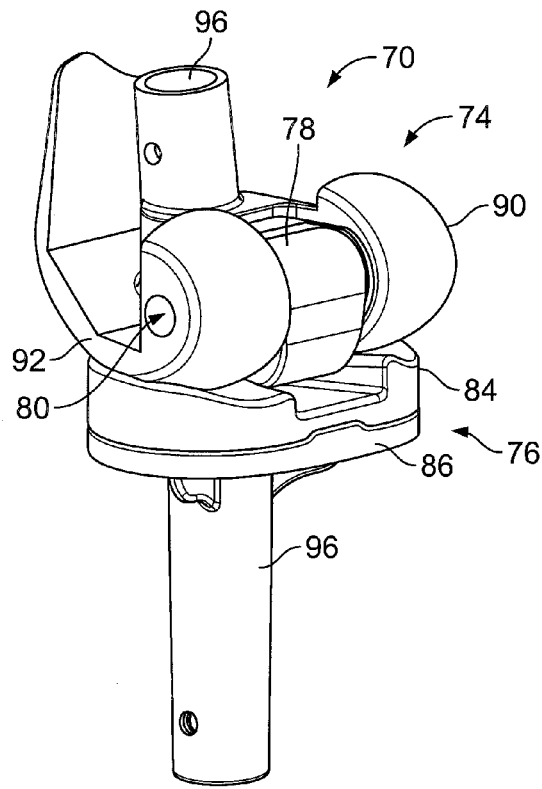
FIG. 5 is an isometric view of an embodiment of a hinged knee.

Turning now to FIGS. 5-8, these FIGs. show views of another embodiment of a hinged knee 70. Turning now to FIG. 5, FIG. 5 is an isometric view of an embodiment of the hinged knee 70. The hinged knee 70 includes a femoral component 74, a tibial component 76, a pin sleeve 78 and a pin 80. The tibial component 76 includes a tibial insert 84 and a tibial base 86. The femoral component 74 includes a medial condyle 90 and a lateral condyle 92. The pin 80 connects the condyles 90 and 92 to the sleeve 78. The sleeve 78 connects to the tibial component through a sleeved post.

As the knee flexes, the femoral component 74 rotates relative to the tibial component 76. The femoral component 74 rotates about the pin 80. Axial rotation and anterior/posterior (A/P) translation of the femoral component 74 is urged by the shape of the tibial insert 84 and the condyles 90 and 92. The axial rotation and anterior/posterior (A/P) translation of the femoral component 74 may occur because the pin 80 is able to axially rotate and be axially translated relative to the post and sleeve of the hinged knee 70.

The femoral component 74 and the tibial component 76 are connected to the femur and tibia, respectively. Stems 96 are inserted into the femur and tibia to fix the femoral component and tibial component to the bones. The length and thickness of these stems may be adjusted based upon required fixation, size of the bones, and size of the intramedullary canals in the bones.

Figure 6:
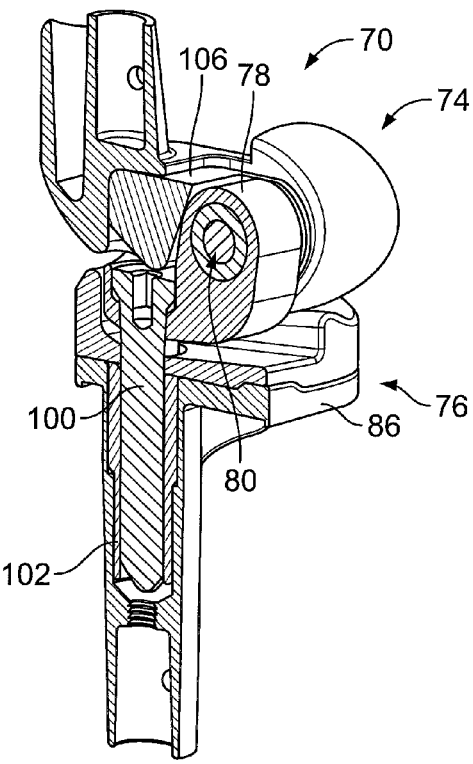
FIG. 6 is a cutaway view of the embodiment of FIG. 5.

Turning now to FIG. 6, FIG. 6 is a cutaway view of the embodiment of FIG. 5. The cutaway is taken in a sagittal plane between the femoral condyles. FIG. 6 shows the pin 80 in the sleeve 78. The sleeve 78 is attached to a post 100 which is inserted into a post sleeve 102. The post sleeve 102 is attached to the tibial base 86. The post 100 may be axially rotated and axially translated relative to the post sleeve 102. The pin sleeve 78 (and thus the pin 80) may rotate axially and translate axially relative to the tibial component 76. The rotation and translation allow for the femoral component 74 to axially rotate and to translate in the A/P direction. The A/P translation may be accomplished by the condyle surface having a curvature with a center of rotation outside the pin 80. As the femoral component 74 rotates, a bushing 106 stops hyper extension so that the knee may not over extend.

Figure 7:
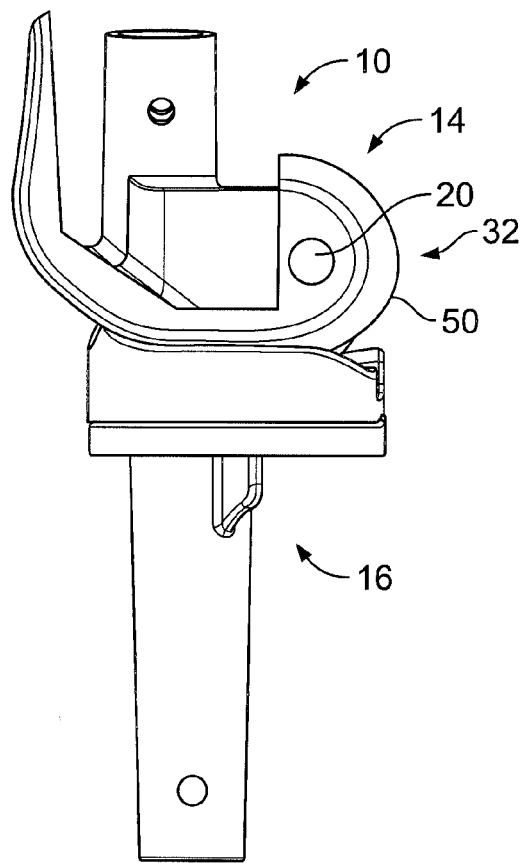
FIG. 7 is a side view of the embodiment of FIG. 5.

Turning now to FIG. 7, FIG. 7 is a side view of the embodiment of FIG. 5. The pin 80 is located posterior to the center of the knee 70. The curve 110 of the condyle 92 is eccentric with respect to the center of rotation of the femoral component 74, which is the pin 80. With respect to the tibial component 76, the pin 80 axially rotates and axially translates as the knee flexes.

Figure 8:
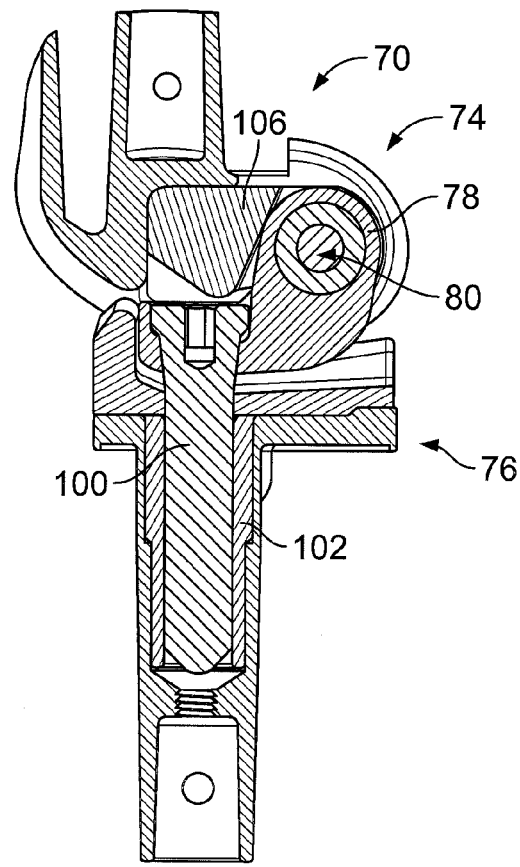
FIG. 8 is a cutaway view of the embodiment of FIG. 7.

Turning now to FIG. 8, FIG. 8 is a cutaway view of the embodiment of FIG. 7. The cutaway is taken along the same sagittal plane of the cutaway in FIG. 6. The cutaway shows the post 100 and post sleeve 102 of the hinged knee 70. An enlarged portion 106 of the post 100 fixes the post 100 to the femoral component 74 so that when the post 100 is inserted in the post sleeve 102, the femoral component 74 is aligned and held in place relative to the tibial component 76. The post 100 and pin sleeve 78 then may rotate and translate axially without pulling the femoral component 74 off the tibial base 76.

Figure 9:
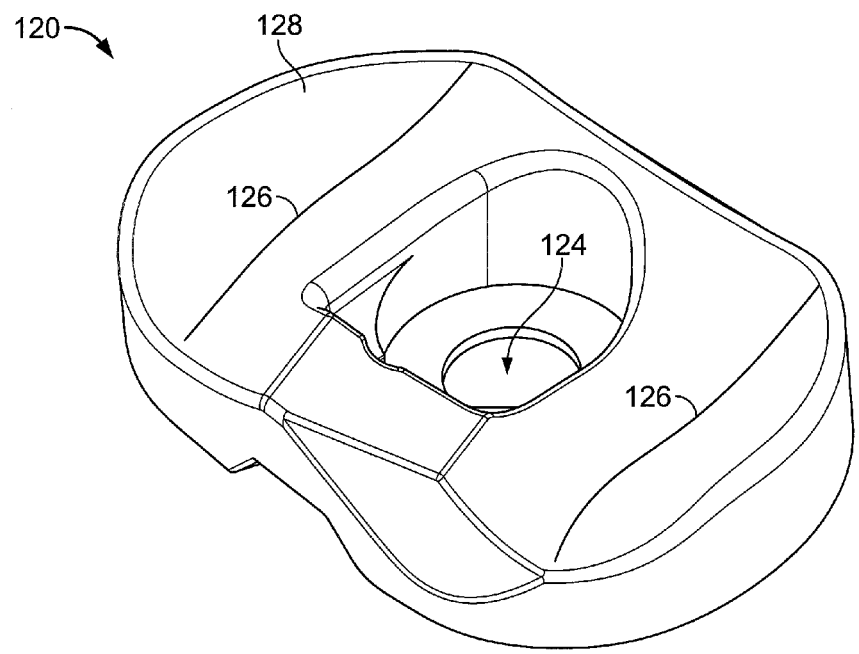
FIG. 9 is an isometric view of an embodiment of a tibial insert.
Figure 10:
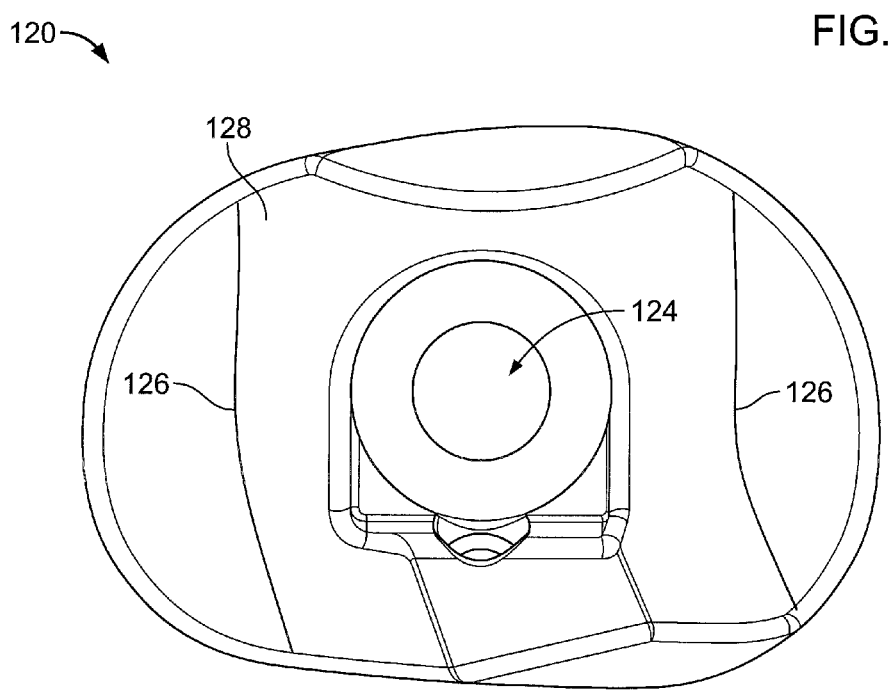
FIG. 10 is a top view of the tibial insert of FIG. 9.

Turning now to FIGS. 9 and 10, these FIGs. show views of a tibial insert 120. FIG. 9 is an isometric view of an embodiment of a tibial insert 120 and FIG. 10 is a top view of the tibial insert 120 of FIG. 9. The tibial insert 120 includes a post hole 124 for receiving the post from either the tibial base or the femoral component. Direction lines 126 on a bearing surface 128 show the lines the femoral component articulates on the tibial insert 120. As the femoral component rotates on the insert 120, the position on the line 126 travels posteriorly. The posterior portion of the tibial insert 120 slopes to axially rotate and translate the femoral component posteriorly. Together in conjunction with the curvature of the condyles, the tibial insert 120 cause A/P translation and axial rotation of the femoral component.

Figure 11:
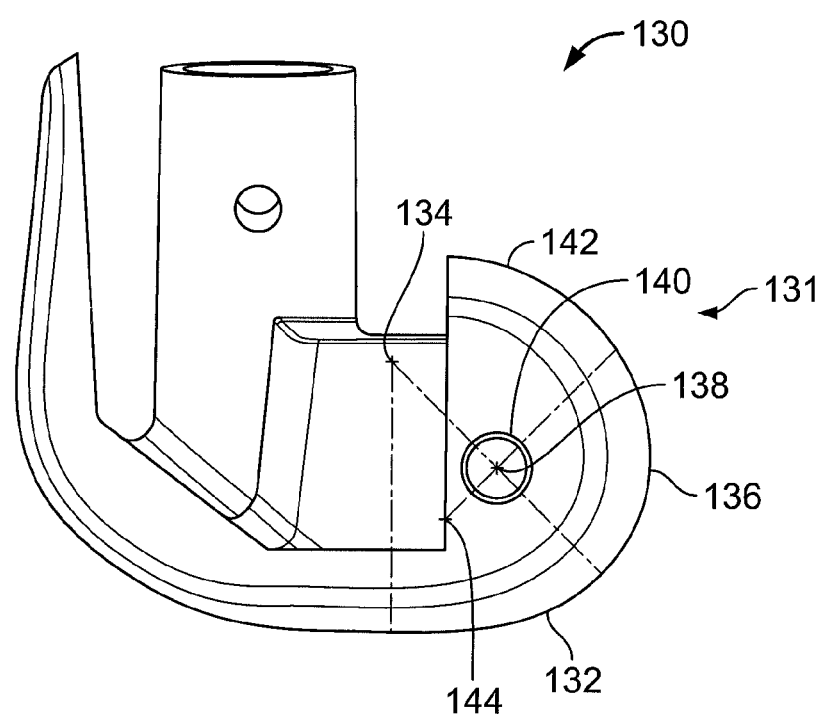
FIG. 11 is a side view of an embodiment of femoral component of a hinged knee.

Turning now to FIG. 11, FIG. 11 is a side view of an embodiment of femoral component 130 of a hinged knee. The curvature of a condyle 131 includes a first distal portion 132 having a first center of rotation 134, a second posterior portion 136 having a second center of rotation 138 concentric with a pin hole 140, and a third proximal portion 142 having a third center of rotation 144. The centers of rotation 134 and 144 are eccentric to the pin hole 140. As the knee rotates, the contact point between the femoral component 130 and the tibial insert produces a force normal to the femoral component 130 and aligned with the center of rotation for that section of the curvature. While the contact point is within the distal portion of the curvature, the normal force points toward the center of rotation 134. At the interface between the distal portion 132 and the posterior portion 136, the normal force is collinear with the centers of rotation 134 and 138. Similarly, At the interface between the posterior portion 136 and the proximal portion 142, the normal force is collinear with the centers of rotation 138 and 144. thus, the contact points do not jump during rotation but smoothly move.

The eccentricity of the curvatures allows for the lateral forces at the contact points to control axial rotation and A/P translation. Because the forces are normal to the tibial and femoral surfaces, reactive forces at the contact points induce A/P motion and axial rotation. The pins, sleeves, and posts of the hinged knee allow for the translation and rotation of the femoral component 130 with respect to the tibial component.

Figure 12:
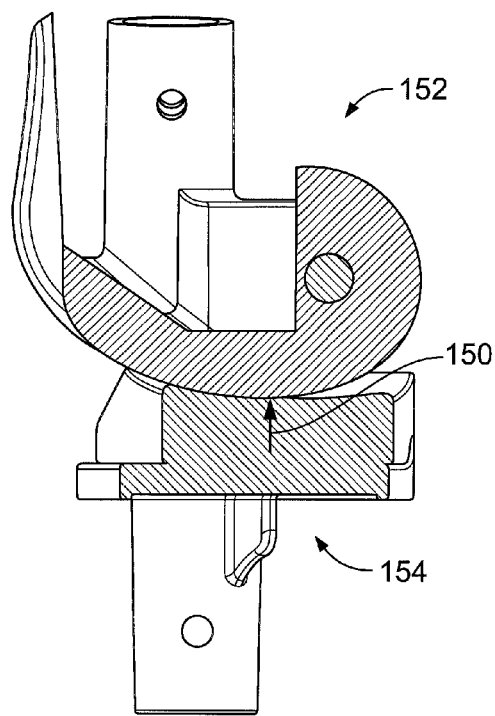
FIGS. 12 and 13 are a side view and an isometric view, respectively, of an embodiment of a hinged knee at extension.
Figure 13:
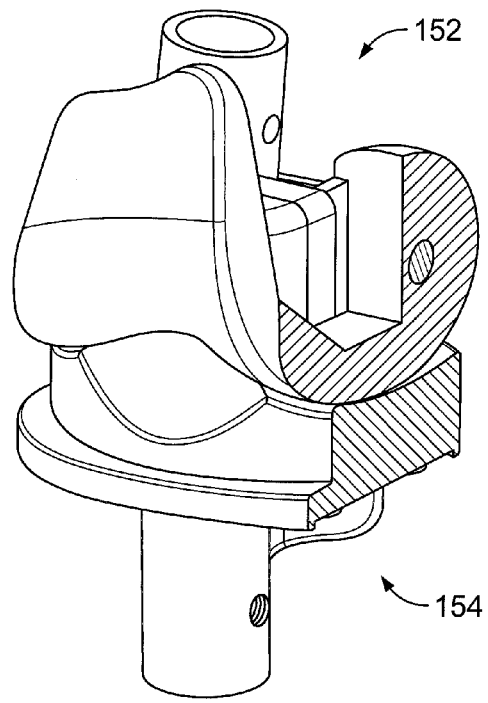

Turning now to FIGS. 12-23, the FIGs. show side views and isometric views of an embodiment of a hinged knee in different angles of flexion. FIGS. 12 and 13 are a side view and an isometric view, respectively, of an embodiment of a hinged knee at extension. A contact point 150 anterior to the pin axis is the contact point between a femoral component 152 and a tibial component 154. The tibial component is posteriorly distal sloped at the contact point 150 so there is a reactive contact force attempting to push the femoral component backwards. FIG. 13 shows the position of the femoral component 152 at extension.

Figure 14:
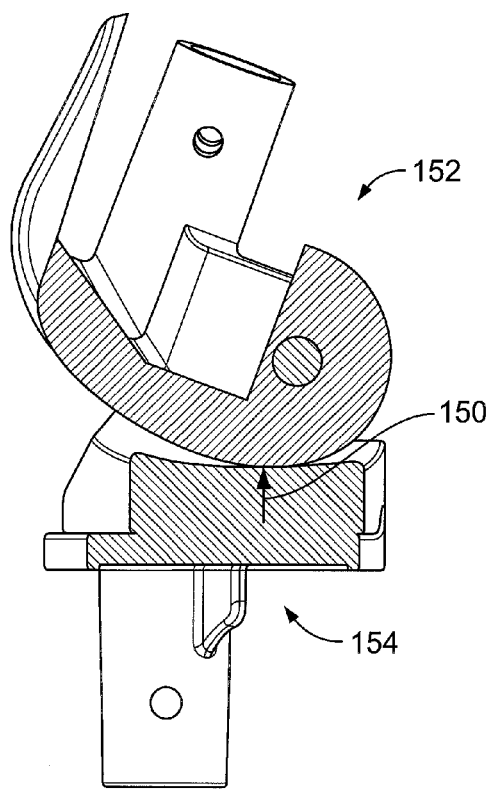
FIGS. 14 and 15 are a side view and an isometric view, respectively, of the hinged knee of FIG. 12 at 20 degrees flexion.
Figure 15:
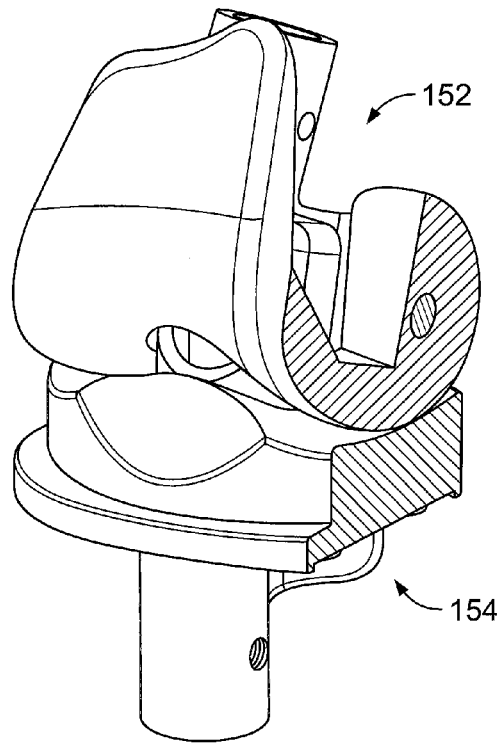

Turning now to FIGS. 14 and 15, FIGS. 14 and 15 are a side view and an isometric view, respectively, of the hinged knee of FIG. 12 at 20 degrees flexion. As the knee flexes, the contact point 150 moves posteriorly. Additionally, as shown in FIG. 15, the femoral component 152 has rotated relative to the tibial component 154. The axial rotation is urged by a differential between the moments created by the reactive forces at the medial and lateral condyles.

Figures 16, 17:
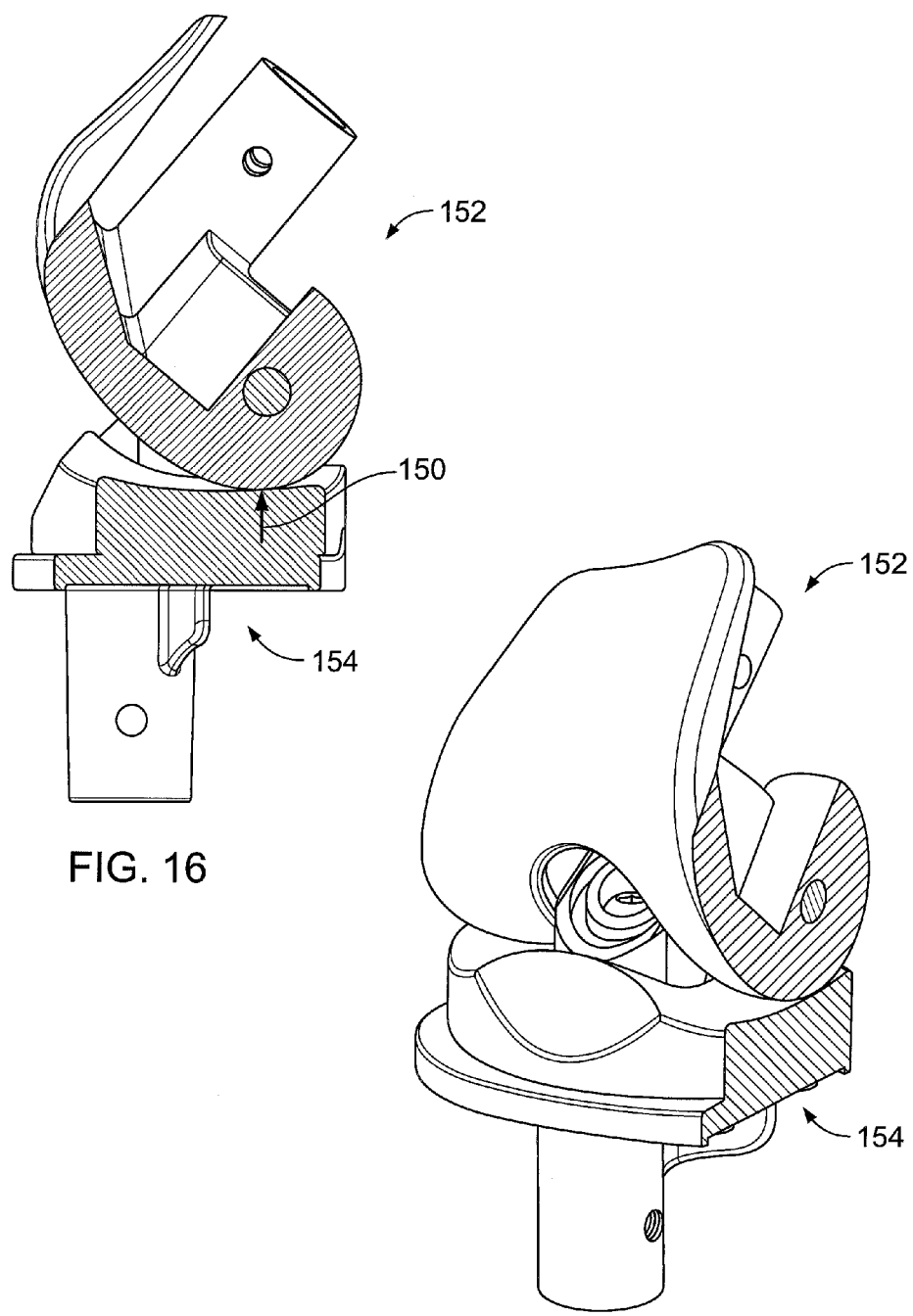
FIGS. 16 and 17 are a side view and an isometric view, respectively, of the hinged knee of FIG. 12 at 40 degrees flexion.

Turning now to FIGS. 16 and 17, FIGS. 16 and 17 are a side view and an isometric view, respectively, of the hinged knee of FIG. 12 at 40 degrees flexion. The contact point 150 has shifted posteriorly and the femoral component has continued to rotate axially. This change in contact point shows the A/P translation of the femoral component as the knee rotates. While most of the motion during early knee flexion is axial rotation, some A/P translation occurs. This "rollback" and rotation is similar to normal joint kinematics. These movements are urged by the shapes of the tibial and femoral component. This minimizes shear forces on the patella which may otherwise try to force these movements of the femoral components. Generation of the shear forces in the patella may cause pain or prosthetic failure.

The contact force 150 is directed through the center of the pin hole as the curvature of the condyle transitions from the distal eccentric portion to the posterior concentric portion discussed with reference to FIG. 11.

Figure 18:
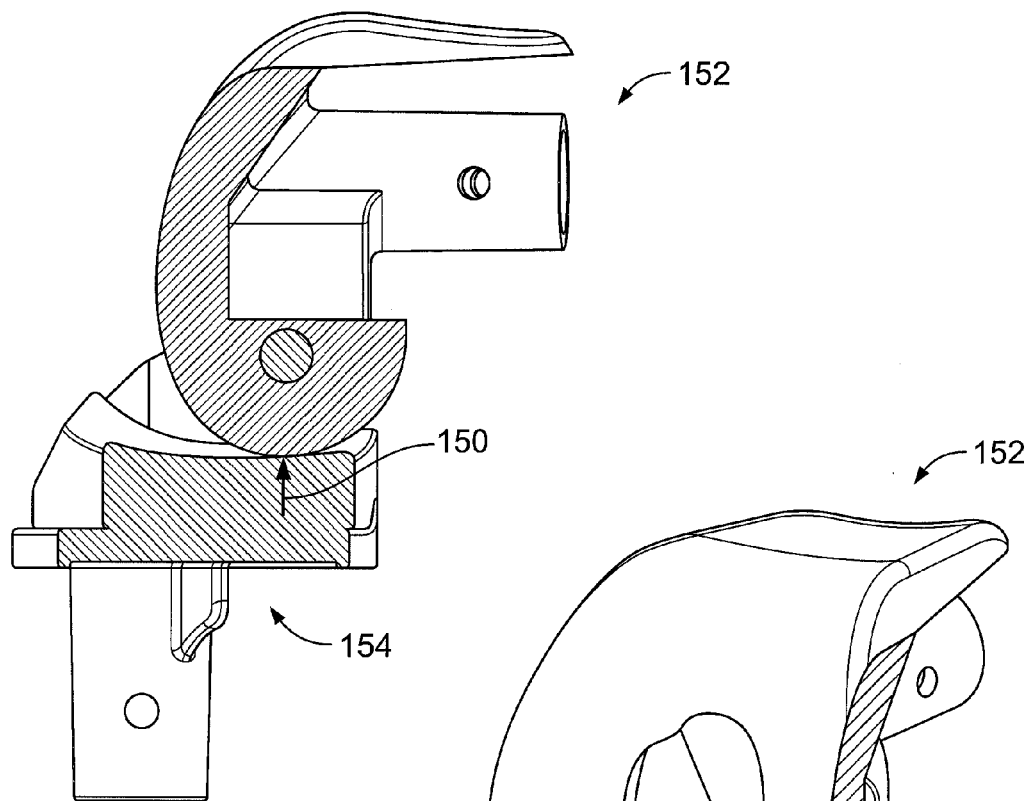
FIGS. 18 and 19 are a side view and an isometric view, respectively, of the hinged knee of FIG. 12 at 90 degrees flexion.
Figure 19:
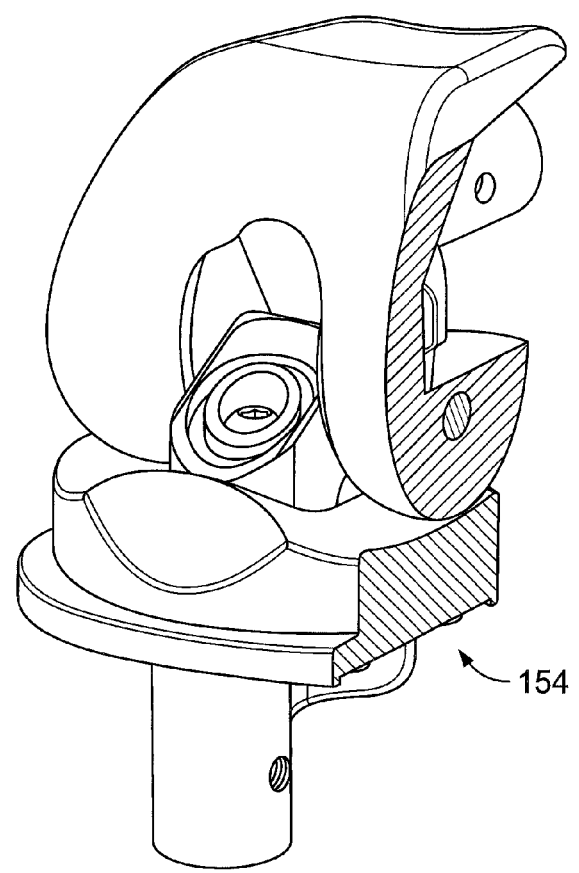

Turning now to FIGS. 18 and 19, FIGS. 18 and 19 are a side view and an isometric view, respectively, of the hinged knee of FIG. 12 at 90 degrees flexion. While flexion continues through the concentric portion, the A/P translation and axial rotation stops. The distance to the center of the pin hole remains constant as the center of curvature for the posterior portion of the condyle is concentric with the pin hole.

Figure 20:
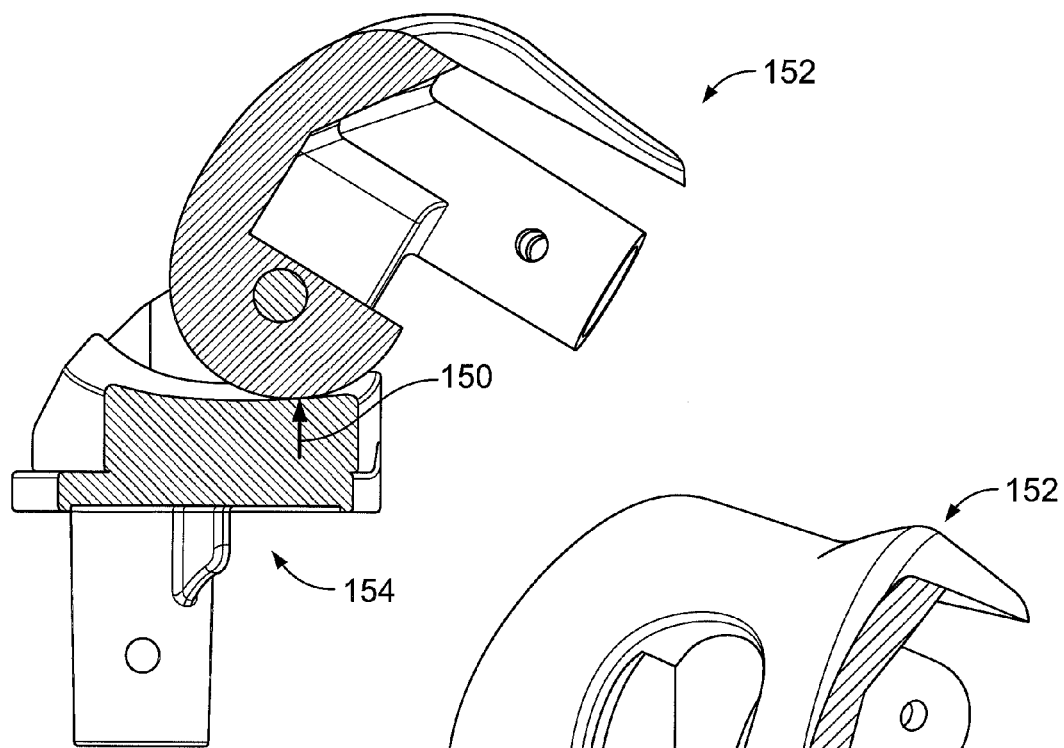
FIGS. 20 and 21 are a side view and an isometric view, respectively, of the hinged knee of FIG. 12 at 120 degrees flexion.
Figure 21:
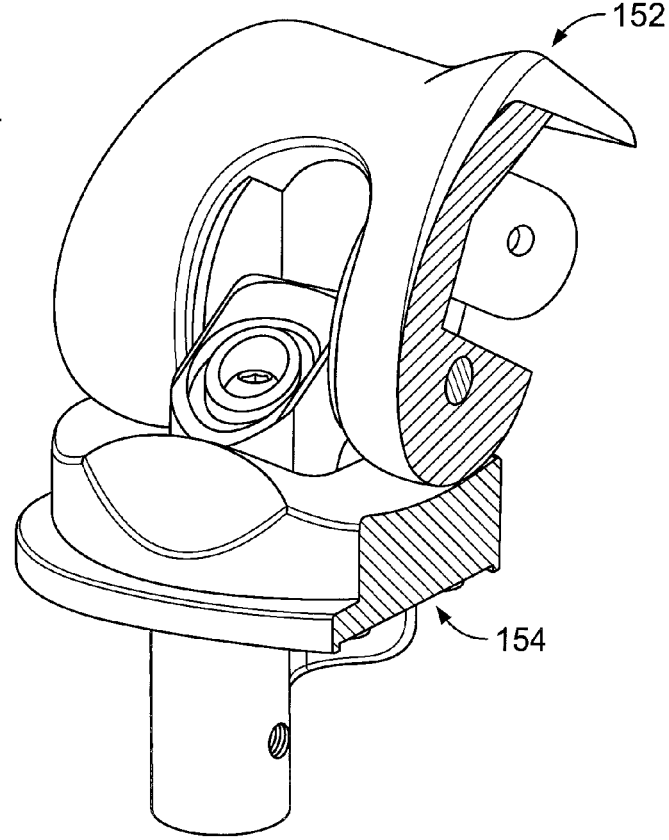

Turning now to FIGS. 20 and 21, FIGS. 20 and 21 are a side view and an isometric view, respectively, of the hinged knee of FIG. 12 at 120 degrees flexion. The contact force 150 is directed through the center of the pin hole as the curvature of the condyle transitions from the posterior concentric portion of the curvature to the proximal eccentric portion discussed with reference to FIG. 11. As the contact force 150 moves posterior the center of the pin hole, the distance from the contact point to the center of the pinhole lessens.

Figures 22, 23:
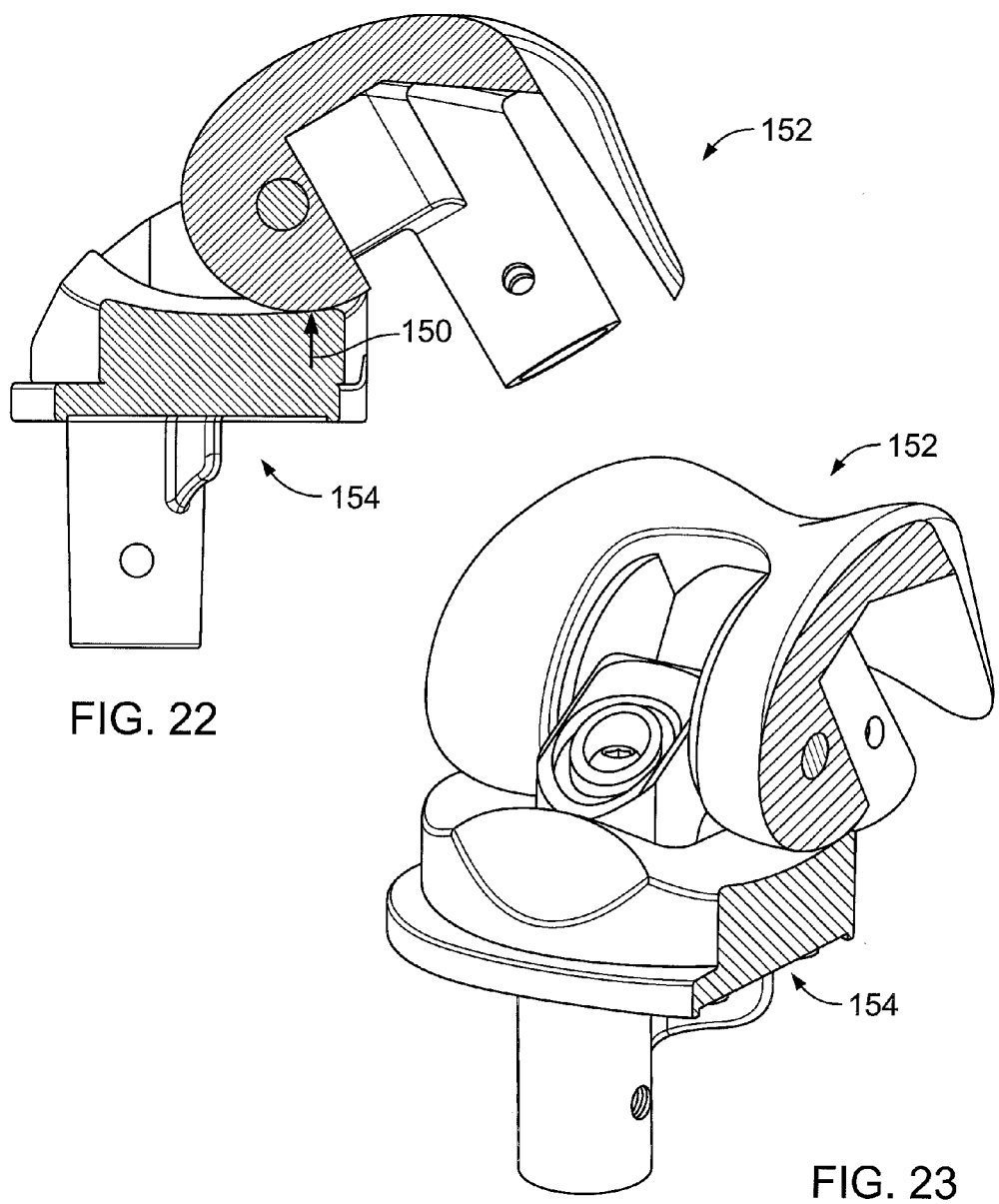
FIGS. 22 and 23 are a side view and an isometric view, respectively, of the hinged knee of FIG. 12 at 150 degrees flexion.

Turning now to FIGS. 22 and 23, FIGS. 22 and 23 are a side view and an isometric view, respectively, of the hinged knee of FIG. 12 at 150 degrees flexion. As the hinged knee continues to rotate, the contact force generally creates A/P translation, and little axial rotation. Again, this is generally consistent with normal knee kinematics. While this embodiment has described A/P translation and axial rotation by surface characteristics of the tibial and femoral components 154 and 152, other embodiments may accomplish these motions in other ways.

The additional embodiments generally try to control lateral forces between the femoral and tibial components. For example, differences in the lateral forces between condyles may create motion. Additionally keeping lateral forces on one side small or zero while controlling the forces on the other side can control axial rotation. For more rotation, forces may be opposite in direction to increase axial rotation. Because rotation is controlled by moments, another method of controlling rotation is to control the moment arms.

Another embodiment may create contact points with corresponding tibial articulation of the femoral articulating surfaces to vary from a plane perpendicular to the transverse axle hinge pin. Generally, the plane would extend through a medial/lateral and/or lateral/medial direction. As the knee moves through the range of motion of the knee, the corresponding insert articulating geometry remains parallel or varies from the same plane creating an axial rotation through whole, in part, and/or various ranges of the range of motion of the joint.

In another embodiment, a concentric sagittal curvature of the medial or lateral femoral condyle's articular surface relative to the transverse hinge pin location and the opposite femoral condyle's articular surface may have eccentric curvature sagittally to the hinge pin location. This shifts the contact with the tibial articulation medial/lateral or lateral/medial at least in part through a range of motion. The tibial articulating surfaces correspond to femoral curvatures and induce axial rotation through whole, in part, and/or various ranges of the range of motion of the joint.

Alternatively, a concentric sagittal curvature of the medial or lateral condyle's articular surface relative to the transverse hinge pin location and the opposite condyle's articular surface having eccentric curvature sagittally to the hinge pin location may create the motion. The tibial articulating surfaces corresponds to femoral curvatures where the corresponding eccentric medial or lateral compartment follows a predetermined path relative to multiple angles of flexion and its corresponding contact points movement. The radial translation of these contact points around the axial rotation around the tibial post/sleeve axis and the corresponding concentric medial or lateral compartment follows a predetermined path relative to multiple angles of flexion and its corresponding contact points movement around the axial rotation around the tibial post/sleeve axis. This induces an axial rotation through whole, in part, and/or various ranges of the range of motion of the joint.

Another embodiment includes a femoral prosthesis with eccentric sagittal curvature for both of the medial and lateral articulating condylar portions of the femoral prosthesis relative to the transverse axle pin position. A tibial insert with the corresponding articulating geometry, either inclining and/or declining as the eccentric contact points of the femoral articulation translates, shift in a medial/lateral and/or lateral/medial direction to induce an axial rotation through whole, in part, and/or various ranges of the range of motion of the joint.

In another embodiment, a concentric sagittal curvature of the medial or lateral condyle's articular surface relative to the transverse hinge pin location and the opposite condyle's articular surface having eccentric curvature sagittally to the hinge pin location. The tibial articulating surfaces correspond to femoral curvatures where the corresponding eccentric medial or lateral compartment follows a predetermined path relative to multiple angles of flexion and its corresponding contact points movement and the radial translation of these contact points around the axial rotation around the tibial post/sleeve axis. The corresponding concentric medial or lateral compartment follows a predetermined inclining and/or declining path relative to multiple angles of flexion and its corresponding contact points movement around the axial rotation around the tibial post/sleeve axis which induces an axial rotation through whole, in part, and/or various ranges of the range of motion of the joint.

Alternatively, a femoral prosthesis with concentric sagital curvature for both of the medial and lateral articulating condylar portions of the femoral prosthesis relative to the transverse pin position. A tibial insert with the corresponding articulating geometry, either inclining and/or declining, form an axial rotating path relative to the femoral articulating surfaces. Translational/rotational freedom allows the transverse pin to rotate and translate the femoral prosthesis.

Figure 24:
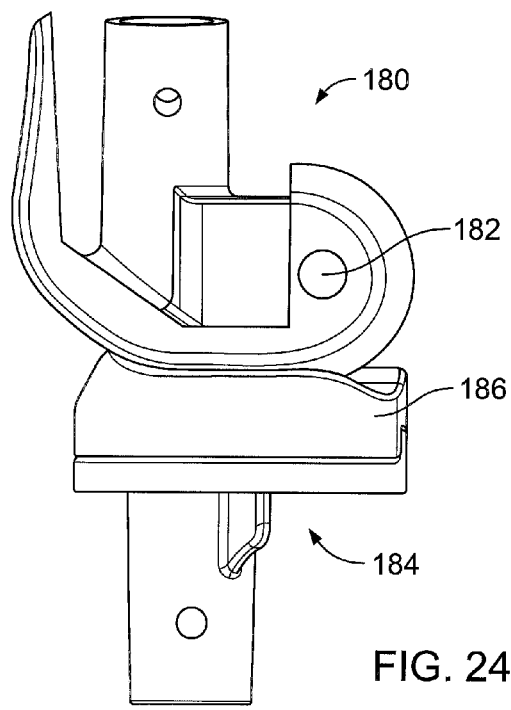
FIGS. 24-26 are a side view, an isometric view, and a top view, respectively, of an embodiment of a hinged knee at extension.
Figure 25:
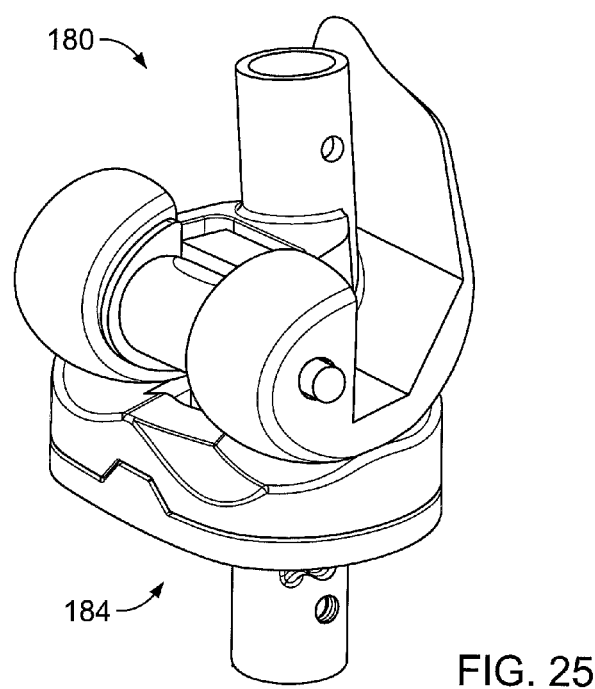
Figure 26:
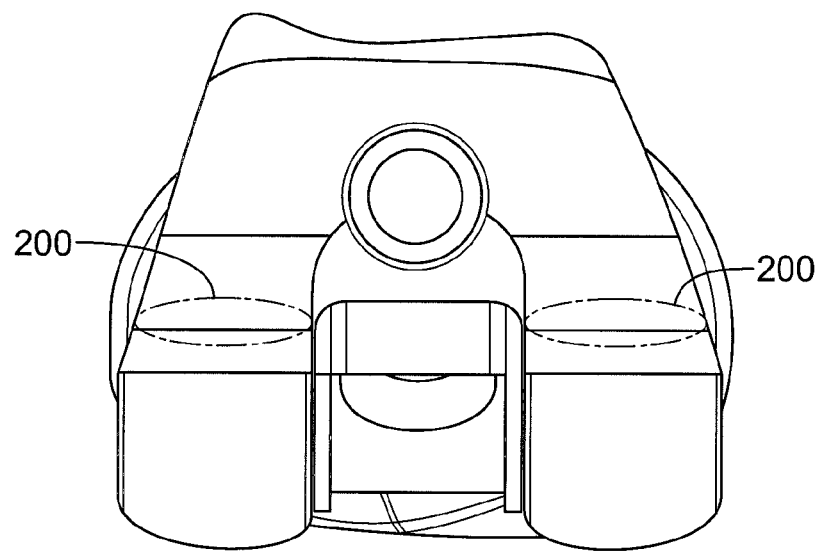

Turning now to FIGS. 24-41, the FIGs. Show side views, isometric views, and top views of an embodiment of a hinged knee in different angles of flexion. FIGS. 24-26 are a side view, an isometric view, and a top view, respectively, of an embodiment of a hinged knee at extension. A femoral component 180 rotates about a pin 182 relative to a tibial component 184. Contact areas 200 show the area in which a tibial insert 186 may contact the femoral component 180. The contact areas 200 in FIGS. 24-41 show how the femoral component 180 rotates and translates along the tibial insert 186.

Figure 27:
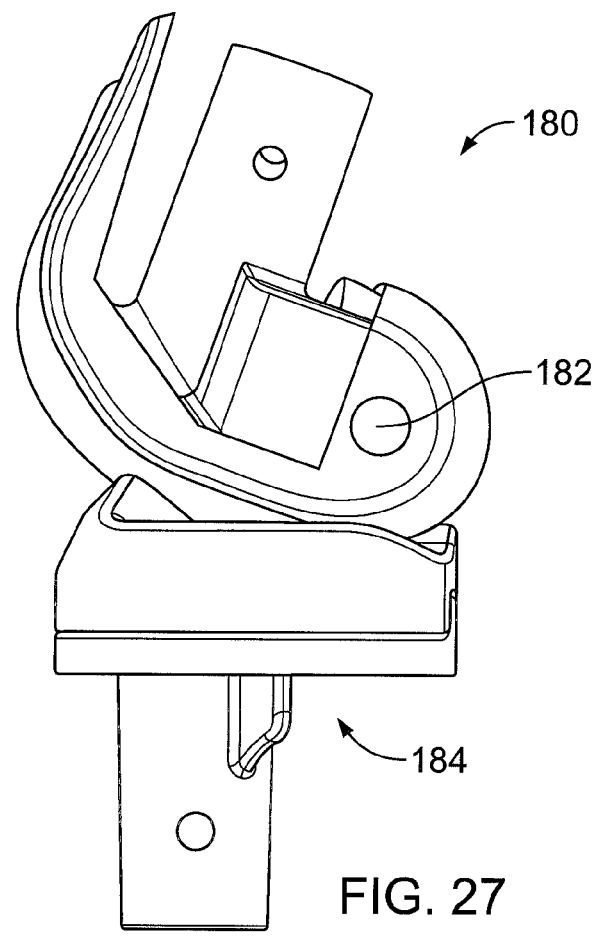
FIGS. 27-29 are a side view, an isometric view, and a top view, respectively, of the hinged knee of FIG. 27 at 20 degrees flexion.
Figure 28:
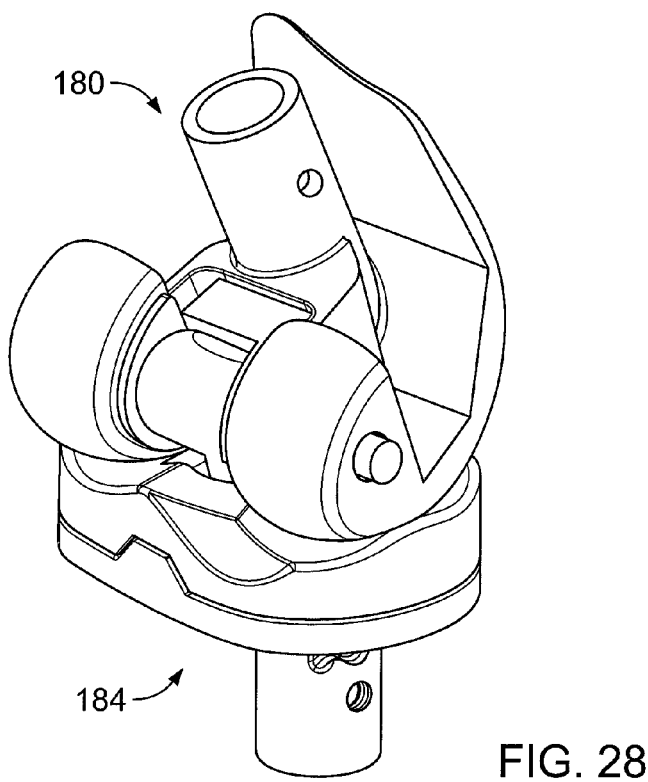
Figure 29:
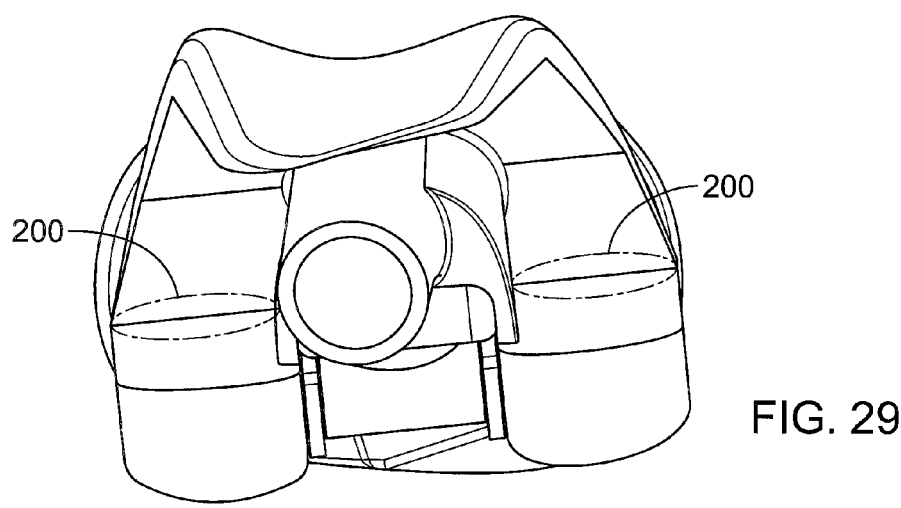

Turning now to FIGS. 27-29, FIGS. 27-29 are a side view, an isometric view, and a top view, respectively, of the hinged knee of FIG. 27 at 20 degrees flexion. The femoral component 180 continues to rotate about the pin 182 relative to the tibial component 184. The contact areas 200, particularly the lateral contact area, have rolled back. The roll back of the lateral contact area corresponds to axial rotation of the femoral component 180 relative to the tibial component 184.

Figure 30:
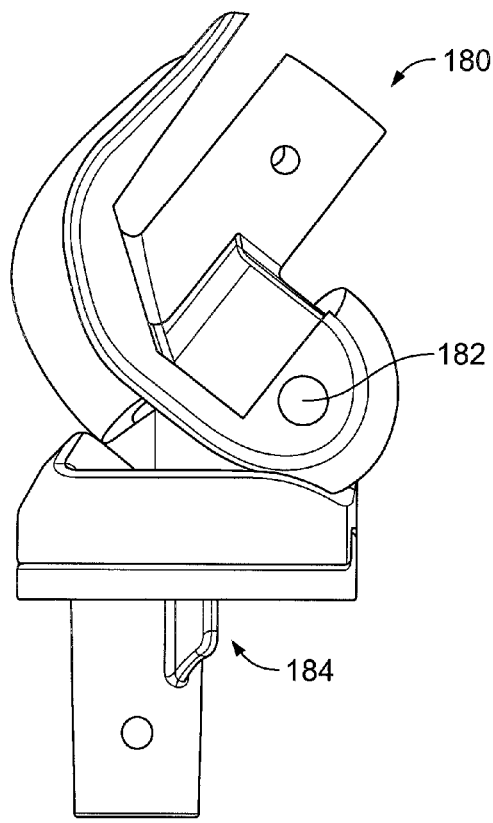
FIGS. 30-32 are a side view, an isometric view, and a top view, respectively, of the hinged knee of FIG. 27 at 40 degrees flexion.
Figure 31:
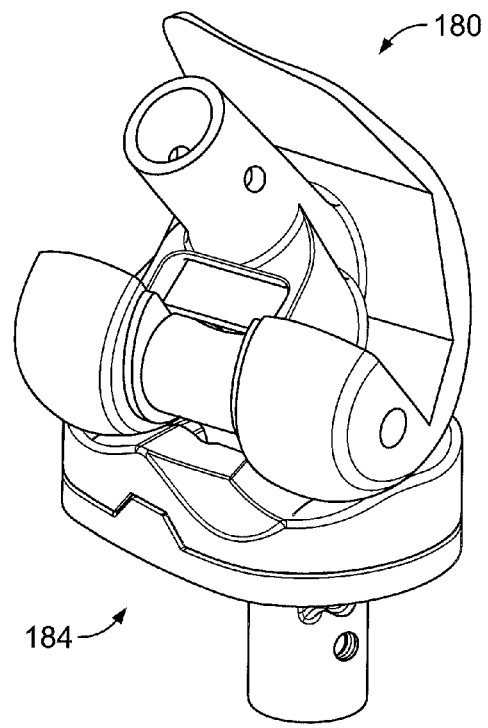
Figure 32:
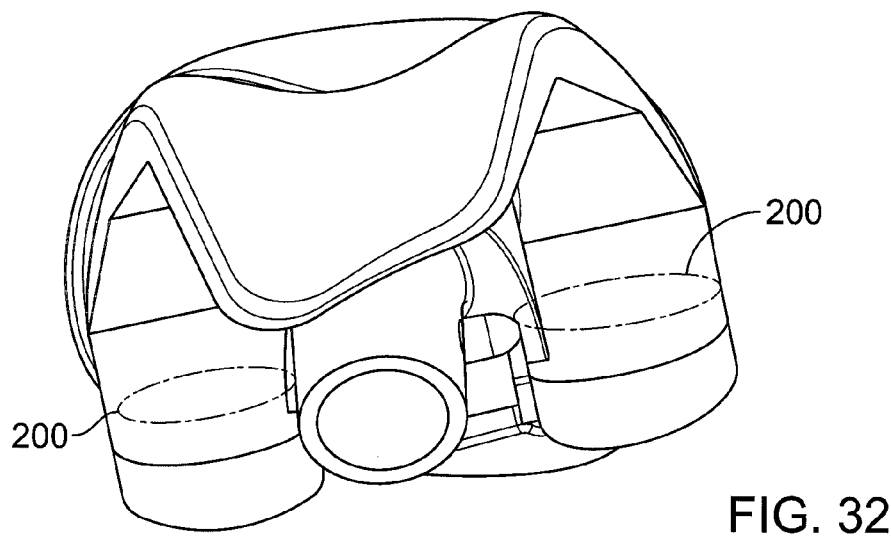

Turning now to FIGS. 30-32, FIGS. 30-32 are a side view, an isometric view, and a top view, respectively, of the hinged knee of FIG. 27 at 40 degrees flexion. The femoral component 180 continues to rotate about the pin 182 relative to the tibial component 184. The contact areas 200 have continued to roll back, and again the lateral contact area has translated farther posteriorly compared to the medial condyle. This corresponds to more axial rotation.

Figure 33:
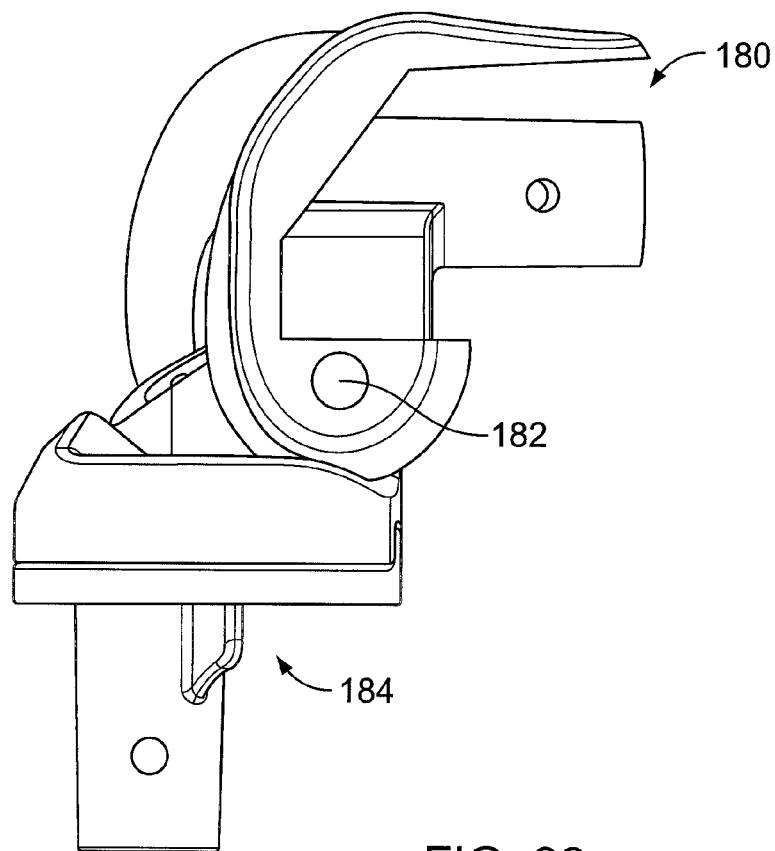
FIGS. 33-35 are a side view, an isometric view, and a top view, respectively, of the hinged knee of FIG. 27 at 90 degrees flexion.
Figure 34:
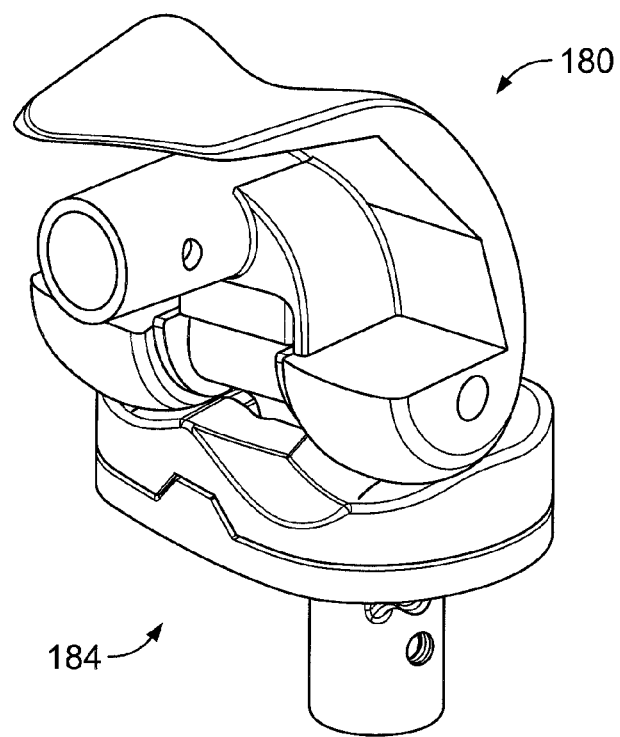
Figure 35:
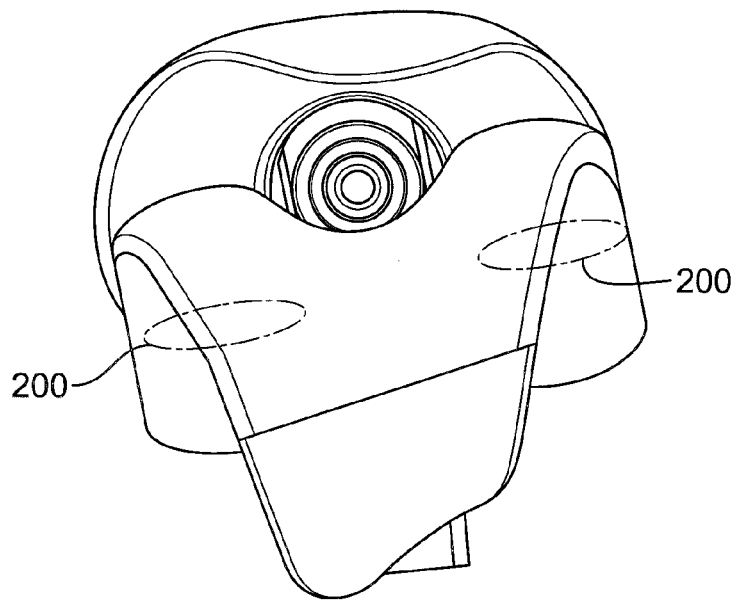

Turning now to FIGS. 33-35, FIGS. 33-35 are a side view, an isometric view, and a top view, respectively, of the hinged knee of FIG. 27 at 90 degrees flexion. The femoral component 180 continues to rotate about the pin 182 relative to the tibial component 184. From 40 degrees to 90 degrees of flexion, the rotation and translation are minimized as the rotation continues through the concentric portion of the curvature.

Figure 36:
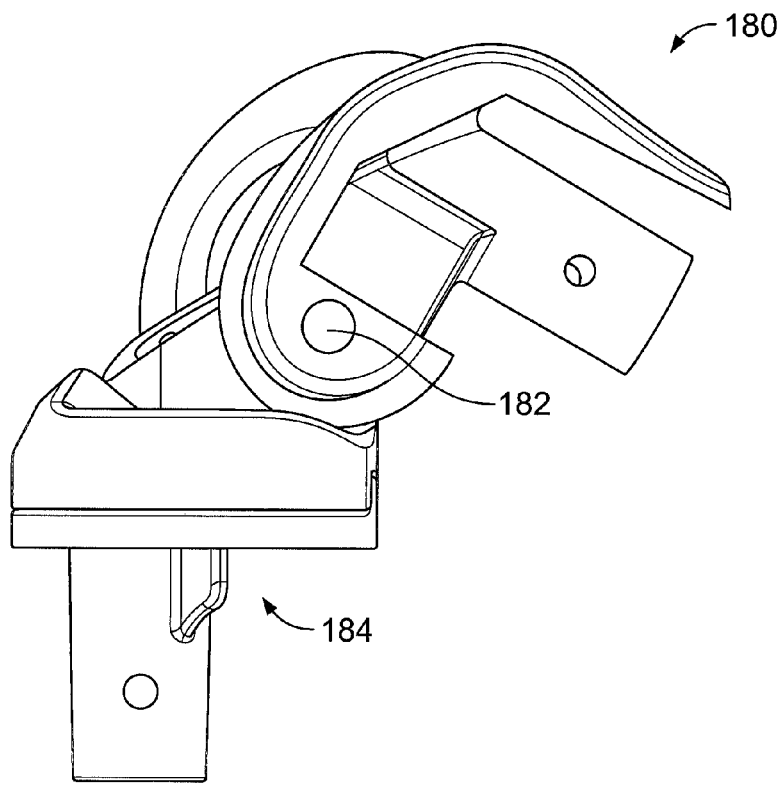
FIGS. 36-38 are a side view, an isometric view, and a top view, respectively, of the hinged knee of FIG. 27 at 120 degrees flexion.
Figure 37:
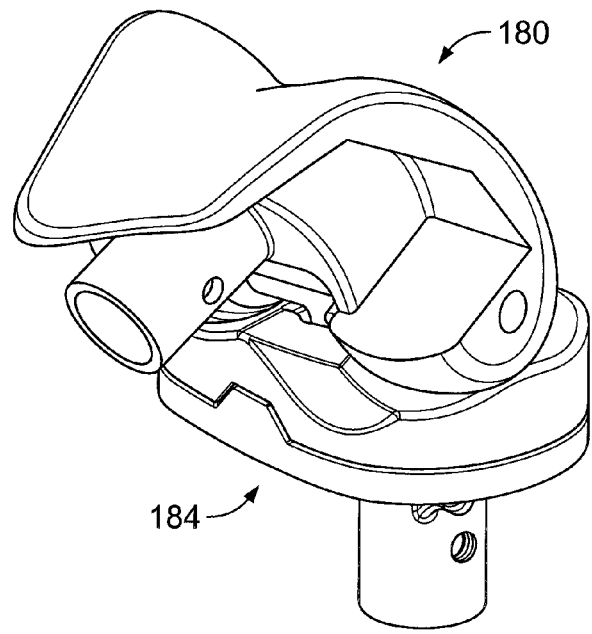
Figure 38:
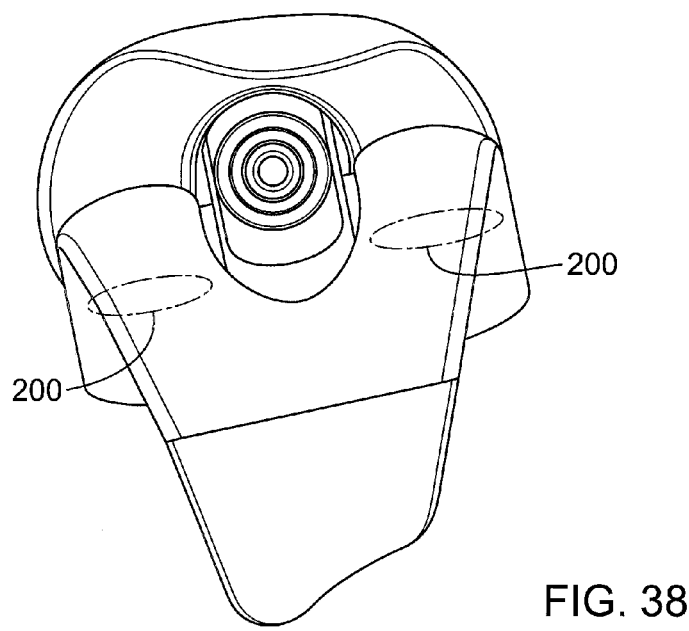

Turning now to FIGS. 36-38, FIGS. 36-38 are a side view, an isometric view, and a top view, respectively, of the hinged knee of FIG. 27 at 120 degrees flexion. The femoral component 180 continues to rotate about the pin 182 relative to the tibial component 184. Similar to the flexion between 40 and 90 degrees, from 90 degrees to 120 degrees of flexion, the rotation and translation are minimized as the rotation continues through the concentric portion of the curvature.

Figure 39:
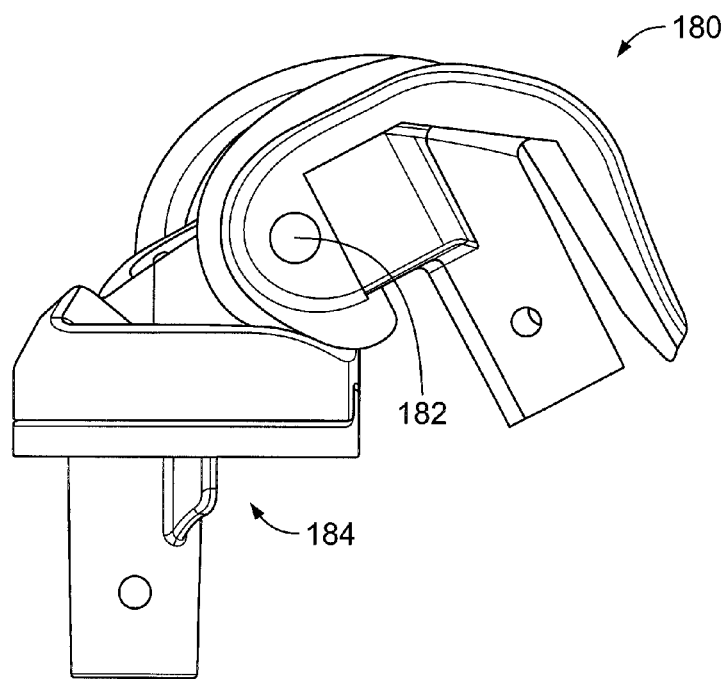
FIGS. 39-41 are a side view, an isometric view, and a top view, respectively, of the hinged knee of FIG. 27 at 150 degrees flexion.
Figure 40:
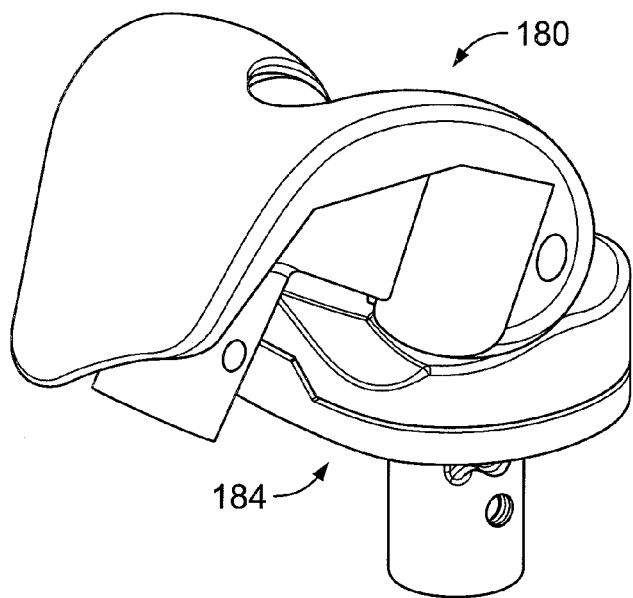
Figure 41:
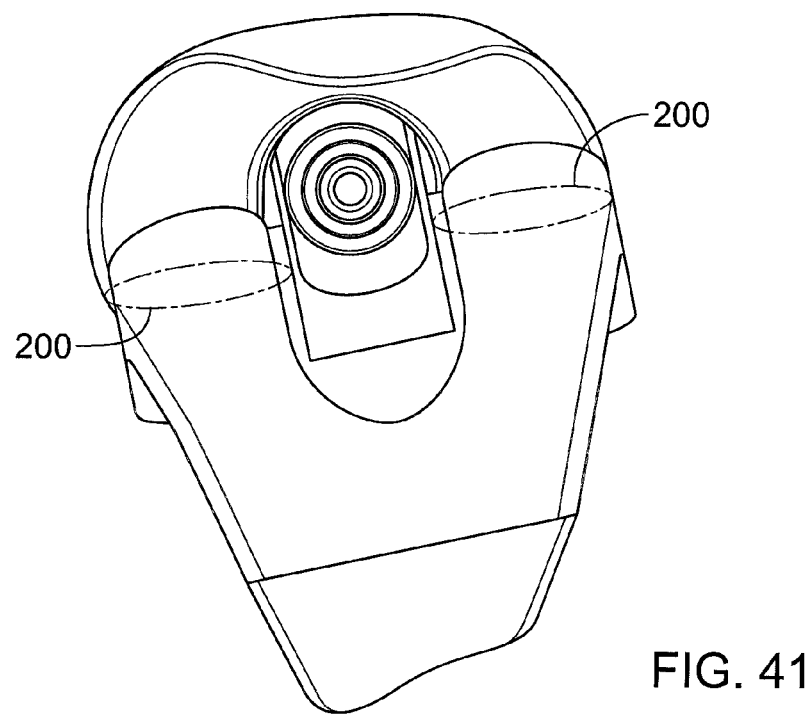

Turning now to FIGS. 39-41, FIGS. 39-41 are a side view, an isometric view, and a top view, respectively, of the hinged knee of FIG. 27 at 150 degrees flexion. The femoral component 180 continues to rotate about the pin 182 relative to the tibial component 184. As the flexion continues from 120 to 150 degrees, the contact areas 200 translate and have little axial rotation.

Thus, as the knee flexes, the rotation allows for the patella to slide along the patellar groove without generating forces in the patella. Additionally, with movement approximating the natural movement, the hinged knee does not generate forces in the soft tissue. This may help preserve soft tissue that is initially damaged by surgery. Moreover, some soft tissue is removed during surgery, and thus the remaining soft tissue must work harder to complete tasks. Reducing the forces on soft tissue can reduce swelling, pain and additional stresses on the soft tissue after surgery.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A hinged knee prosthesis, comprising:
   a. a tibial component configured to attach to a tibia, the tibial component having a bearing surface with a posterior portion, the posterior portion including medial and lateral posterior portions each having a contour that slopes medially in a posterior direction, the tibial component having a superior-inferior axis; and
   b. a femoral component configured to hingedly attach to the tibial component and axially rotate relative to the tibial component about the superior-inferior axis, the femoral component comprising:
      i. a medial condyle; and
      ii. a lateral condyle, the medial and lateral condyles having a sagittal curvature surface configured to contact the bearing surface and induce axial rotation of the femoral component relative to the bearing surface of the tibial component when the medial and lateral condyles are in contact with the posterior portion of the tibial component and the femoral component is moving in a posterior direction relative to the tibial component.

2. The hinged knee prosthesis of claim 1, wherein the medial and lateral condyles have a plurality of eccentric sagittal curvature surfaces configured to rotate on the bearing surface of the tibial component.

3. The hinged knee prosthesis of claim 2, wherein the center of rotation of a first eccentric sagittal curvature surface of the medial condyle is not aligned with the center of rotation of a first eccentric sagittal curvature surface of the lateral condyle, wherein the medial and lateral condyles direct axial rotation and anterior/posterior translation of the femoral component relative to the tibial component when the first eccentric sagittal curvature surfaces contact the tibial component, and wherein the center of rotation of a second eccentric sagittal curvature surface of the medial condyle is aligned with the center of rotation of a second eccentric sagittal curvature surface of the lateral condyle, wherein the medial and lateral condyles direct anterior/posterior translation of the femoral component relative to the tibial component when the second eccentric sagittal curvature surfaces contact the tibial component.

4. The hinged knee prosthesis of claim 1, wherein the posterior portion of the bearing surface is configured to guide the medial and lateral condyles of the femoral component such that contact points between the femoral component and the tibial component translate in the anterior/posterior direction and rotate axially relative to the bearing surface.

5. The hinged knee prosthesis of claim 1, further comprising an axle hinge pin, the axle hinge pin located transversely between the medial and lateral condyles.

6. The hinged knee prosthesis of claim 5, further comprising a post configured to extend from the tibial component to the femoral component, a proximal portion of the post configured to attach to the axle hinge pin.

7. The hinged knee prosthesis of claim 6, further comprising a sleeve configured to receive the post, the sleeve configured to allow axial rotation of the femoral component relative to the tibial component.

8. The hinged knee prosthesis of claim 7, wherein the post attaches to the axle hinge pin via a screw such that the post sleeve can move relative to the post.

9. The hinged knee prosthesis of claim 7, wherein the post attaches to the axle hinge pin via a pin sleeve such that the post can move relative to the post sleeve.

10. The hinged knee prosthesis of claim 7, wherein the axle hinge pin is configured to rotate relative to the bearing surface about the post.

11. The hinged knee prosthesis of claim 1, wherein the medial condyle of the femoral component further comprises a concentric sagittal curvature surface wherein the center of rotation of the concentric sagittal curvature surface of the medial condyle is not aligned with the center of rotation of a portion of an eccentric sagittal curvature surface of the lateral condyle, wherein the medial and lateral condyles direct axial rotation of the femoral component relative to the tibial component.

12. The hinged knee prosthesis of claim 1, wherein the medial and lateral condyles each have an eccentric sagittal curvature surface having a center of rotation not aligned with the axle hinge pin.

13. The hinged knee prosthesis of claim 12, wherein the center of rotation of a portion of the eccentric sagittal curvature surface of the medial condyle is not aligned with the center of rotation of a portion of the eccentric sagittal curvature surface of the lateral condyle, wherein the medial and lateral condyles direct axial rotation of the femoral component relative to the tibial component.

14. The hinged knee prosthesis of claim 12, wherein the center of rotation of a portion of the eccentric sagittal curvature surface of the medial condyle is aligned with the center of rotation of a portion of the eccentric sagittal curvature surface of the lateral condyle, wherein the medial and lateral condyles direct anterior/posterior translation of the femoral component relative to the tibial component.

15. The hinged knee prosthesis of claim 1, wherein the bearing surface is shaped to translate the lateral condyle farther posterior than the medial condyle during flexion of the hinged knee prosthesis.

16. The hinged knee prosthesis of claim 1, wherein the tibial component comprises a tibial insert and a tibial base, wherein the tibial insert remains at a fixed position relative to the tibial base during flexion of the hinged knee prosthesis.

17. The hinged knee prosthesis of claim 1, wherein the medial condyle is configured to contact the bearing surface at medial contact points and the lateral condyle is configured to contact the bearing surface at lateral contact points, and wherein the posterior portion of the bearing surface is sloped to guide translation of the lateral contact points farther posterior than the medial contact points during flexion of the hinged knee prosthesis.

18. The hinged knee prosthesis of claim 1, wherein the sagittal curvature surface of the medial and lateral condyles is configured to induce the axial rotation through contact with the contours of the medial and lateral posterior portions that slope medially in the posterior direction.

19. A hinged knee prosthesis, comprising:
   a. a tibial component configured to attach to a tibia, the tibial component comprising a tibial insert and a tibial base, the tibial insert having a bearing surface with a posterior portion, the posterior portion including medial and lateral posterior portions each having a contour that slopes medially in a posterior direction, the tibial component having a superior-inferior axis; and
   b. a femoral component configured to hingedly attach to the tibial component and axially rotate relative to the tibial component about the superior-inferior axis, the femoral component comprising:
      i. a medial condyle; and
      ii. a lateral condyle, the medial and lateral condyles having a sagittal curvature surface configured to contact the bearing surface and induce axial rotation of the femoral component relative to the bearing surface of the tibial insert when the medial and lateral condyles are in contact with the posterior portion of the tibial component, the femoral component is moving in a posterior direction relative to the tibial component, and the tibial insert remains stationary relative to the tibial base.

20. A hinged knee prosthesis, comprising:
   a. a tibial component configured to attach to a tibia, the tibial component having a bearing surface with a posterior portion, the posterior portion including medial and lateral posterior portions each having a contour that slopes medially in a posterior direction, the tibial component having a superior-inferior axis; and
   b. a femoral component configured to hingedly attach to the tibial component and axially rotate relative to the tibial component about the superior-inferior axis, the femoral component comprising:
      i. a medial condyle; and
      ii. a lateral condyle, the medial and lateral condyles having a sagittal curvature surface configured to contact the bearing surface and induce axial rotation of the femoral component relative to the bearing surface of the tibial component when the medial and lateral condyles are in contact with the posterior portion of the tibial component and the femoral component is moving in a posterior direction relative to the tibial component,
   wherein the posterior portion of the bearing surface is shaped to guide the lateral condyle more posteriorly than the medial condyle during flexion of the hinged knee prosthesis.

* * * * *

UNITED STATES PATENT AND TRADEMARK OFFICE
CERTIFICATE OF CORRECTION

PATENT NO. : 8,523,950 B2  
APPLICATION NO. : 12/307102  
DATED : September 3, 2013  
INVENTOR(S) : Roger Ryan Dees, Jr., Paul Charles Crabtree, Jr. and Jonathan Kirk Nielsen It is certified that error appears in the above-identified patent and that said Letters Patent is hereby corrected as shown below:

On the title page item 75 Inventors, replace "Hesbit" with –Nesbit–.

On page 2, item 56 under "Other Publications", replace "Endoprothesis" with –Endoprosthesis–.

In the claims

At Claim 12, Col. 11, line 30, replace "Claim 1," with –Claim 4,–.

Signed and Sealed this  
Fifteenth Day of March, 2016

Michelle K. Lee  
*Director of the United States Patent and Trademark Office*